(12) United States Patent
Yamazaki

(10) Patent No.: US 6,264,634 B1
(45) Date of Patent: Jul. 24, 2001

(54) IMPLANT TYPE CHEMICAL SUPPLY DEVICE

(75) Inventor: Ko Yamazaki, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/121,807

(22) Filed: Jul. 23, 1998

(51) Int. Cl.$^7$ ............................................. A61M 5/142
(52) U.S. Cl. ........................... 604/131; 128/DIG. 12; 604/153; 604/154; 604/891.1
(58) Field of Search .................... 604/154, 151, 604/131, 123, 141, 891.1, 153; 128/DIG. 12, DIG. 13

(56) References Cited

U.S. PATENT DOCUMENTS

| | | | |
|---|---|---|---|
| 3,964,479 | * 6/1976 | Boag et al. ........................ | 604/123 |
| 4,565,600 | * 1/1986 | Jeensalute et al. ................ | 604/123 |
| 4,714,462 | * 12/1987 | DiDomenico .................... | 604/141 |
| 4,758,228 | * 7/1988 | Williams ........................... | 604/123 |
| 4,840,620 | * 6/1989 | Kobayashi et al. ................ | 604/131 |
| 4,898,582 | * 2/1990 | Faste ................................. | 604/141 |
| 5,352,201 | * 10/1994 | Jemmott ............................ | 604/131 |
| 5,514,103 | * 5/1996 | Srisathapat et al. .............. | 604/131 |
| 5,752,930 | * 5/1998 | Risk et al. ........................ | 604/891.1 |
| 5,814,019 | * 9/1998 | Steinbach et al. ................ | 604/131 |

\* cited by examiner

*Primary Examiner*—Paul J. Hirsch
(74) *Attorney, Agent, or Firm*—Adams & Wilks

(57) ABSTRACT

An implant-type chemical supply device includes: a supply tube for supplying chemicals from a chemical tank; a pump unit having an actuating lever which is rotated by a step motor and has rollers on both ends thereof so that the rollers are arranged in contact with the halfway of the supply tube, for extruding the chemicals within the supply tube by the rollers to supply the chemicals; a waveform synthesizing circuit for producing drive pulse groups each having a different effective power; a drive circuit for supplying any one of the drive pulse groups to the step motor in synchronism with a time signal; a detection circuit for generating a non-rotation signal when an induced voltage developed in the drive coil within the step motor by free oscillations of the step motor is equal to or less than a given value after the drive pulse is supplied to the step motor; and a control circuit for controlling the drive circuit so that the drive pulse having an effective power larger by one in magnitude than that of the drive pulse during non-rotation is supplied to the step motor when the non-rotation signal is generated, and the drive pulse having an effective power smaller by one in magnitude than that of the past drive pulse during non-rotation is supplied to the step motor when no non-rotation signal is generated for a predetermined period of time.

2 Claims, 24 Drawing Sheets

FIG. 26

| "+" INPUT TERMINAL | "−" INPUT TERMINAL | Enable TERMINAL | OUTPUT TERMINAL |
|---|---|---|---|
| − | − | 0 | − |
| $V_+ > V_-$ | | 1 | "H" |
| $V < V_-$ | | 1 | "L" |

FIG. 27

| | PULSE WIDTH | CURRENT | TORQUE | PULSE OCCURRENCE RATE |
|---|---|---|---|---|
| P₁ | 4.88 msec. | 320 μA | 80 gcm | 87.0% |
| | 5.86 msec. | 370 μA | 90 gcm | 10.0% |
| | 6.84 msec. | 420 μA | 100 gcm | 2.8% |
| | 7.82 msec. | 460 μA | 110 gcm | 0.2% |
| | 8.79 msec. | 500 μA | 115 gcm | 0% |
| P₂ | 11.7 msec. | 570 μA | 130 gcm | 0.2% |

IMPLANT TYPE CHEMICAL SUPPLY DEVICE

BACKGROUND OF THE INVENTION

1. Field of the Invention

The present invention relates to an implant-type chemical supply device that is implanted in a body, for gradually supplying chemicals to the affected part.

2. Description of the Related Art

An implant-type chemical supply device that supplies chemicals to the affected part is generally made up of a chemical tank, a pump unit, a drive control circuit for the pump unit, and a battery for operation of the device, and supplies the chemicals within the chemical tanks to the affected part through a tube.

The pump unit is structured in such a manner that a part of the tube connected to the chemical tank is U-shaped, and rollers on both ends of an actuating lever are in contact with the tube at a predetermined pressure. The actuating lever is rotationally driven by a step motor to extrude chemicals within the tube in the same direction, and the chemicals are supplied to the affected part by this pressure.

The step motor is driven in such a manner that a dividing signal obtained by sequentially dividing an oscillation signal from an oscillating circuit by a frequency dividing circuit is converted by a pulse synthesizing circuit into two signals which are, for example, 10 msec in pulse width, 62.5 msec in period and 31.25 msec in phase difference, whereby inversion pulses of a current whose flowing direction is changed every 31.25 msec are supplied to a coil of the step motor, and a rotor magnetized to two polarities is sequentially rotated every 180 degrees.

By the way, a drive pulse width (10 msec in the above example), a coil resistance, the number of winding of the coil, the dimensions of the respective portions of the step motor, etc., are designed in such a manner that the step motor can be driven stably even in any predicted circumstances with which the device may encounter. The predicted circumstances include a case in which at least only one roller is pressed for rotating while the roller is pressed against the tube, and a case in which at least two rollers are pressed against the tube. The rollers are redesigned as to rotate while the maximum number of rollers is pressed against the tube. Further, because the step motor is so designed as to be driven stably even if the circumstances such as the hardness of the tube, the viscosity of chemicals or the like are different, a drive pulse having an effective power of a certain level or more is supplied to the coil of the step motor even when a large output torque is not required.

Therefore, in the case where the step motor is low in load, a useless energy is supplied to the step motor from the battery, resulting in reduction of the lifetime of the battery.

SUMMARY OF THE INVENTION

The present invention has been made to solve the problems with the conventional device, and therefore an object of the present invention is to provide an implant-type chemical supply device in which a step motor is driven according to pulses corresponding to a load state of a pump unit that supplies chemicals, so that power consumption can be lowered to thereby elongate the lifetime of the battery.

In order to achieve the above object, according to the present invention, there is provided an implant-type chemical supply device, comprising: a supply tube for supplying chemicals from a chemical tank; a pump unit having an actuating lever which is rotated by a step motor and has rollers on both ends thereof so that the rollers are arranged in contact with the halfway of the supply tube, for extruding the chemicals within the supply tube by the rollers to supply the chemicals; a waveform synthesizing circuit for producing drive pulse groups each having a different effective power; a drive circuit for supplying any one of the drive pulse groups to the step motor in synchronism with a time signal; a detection circuit for generating a non-rotation signal when an induced voltage developed in the drive coil within the step motor by free oscillations of the step motor is equal to or less than a given value after the drive pulse is supplied to the step motor; and a control circuit for controlling the drive circuit so that the drive pulse having an effective power larger by one in magnitude than that of the drive pulse during non-rotation is supplied to the step motor when the non-rotation signal is generated, and the drive pulse having an effective power smaller by one in magnitude than that of the past drive pulse during non-rotation is supplied to the step motor when no non-rotation signal is generated for a predetermined period of time.

Also, according to the present invention, there is provided an implant-type chemical supply device, comprising: a supply tube a part of which is disposed in the form of an arc to form an arcuate portion; a pump unit for supplying chemicals from a chemical tank having an actuating lever which is rotated by a step motor and has rollers on both ends thereof so that the rollers are arranged to be in contact with the arcuate portion of the supply tube only in a range of predetermined angles when the actuating lever is rotated, for extruding the chemicals within the supply tube by the rollers to supply the chemicals; a waveform synthesizing circuit for producing drive pulse groups each having a different effective power; a drive circuit for supplying any one of the drive pulse groups to the step motor in synchronism with a time signal; a detection circuit for generating a non-rotation signal when an induced voltage developed in the drive coil within the step motor by free oscillations of the step motor is equal to or less than a given value after the drive pulse is supplied to the step motor; a timer circuit for outputting a light-load signal indicative of a period of time when the rollers are apart from the supply tube in response to the non-rotation signal; and a control circuit for controlling the drive circuit so that the drive pulse having a larger effective power is supplied to the step motor when no light-load signal is outputted, and the drive pulse having a smaller effective power is supplied to the step motor when the light-load signal is outputted.

In the case where any one of the drive pulse groups is supplied to the step motor, when the non-rotation signal is outputted, the drive pulse having the effective power larger by one. On the other hand, when no non-rotation signal is outputted, the drive pulse having the effective power smaller by one. As a result, the drive pulse having an appropriate effective power suited for the load of the step motor is outputted so that the step motor is operated with the minimum power consumption, thereby being capable of remarkably elongating the lifetime of the battery.

Also, in the structure in which the light-load signal is obtained by the timer circuit, since the drive pulse small in effective power and the drive pulse large in effective power are simply and surely changed over regardless of the presence/absence of the non-rotation signal, the effective power of the drive pulse can be properly changed according to a periodic change in the load of the actuating lever without being adversely affected by a noise signal or the like.

BRIEF DESCRIPTION OF THE DRAWINGS

FIG. 26 is a diagram showing the operation state of the comparator within the detecting circuit;

FIG. 27 is a diagram showing circumstances where the respective drive pulses are generated when the step motor is driven.

DETAILED DESCRIPTION OF THE PREFERRED EMBODIMENTS

Now, a description will be given in more detail of preferred embodiments of the present invention with reference to the accompanying drawings.

Figure 1:
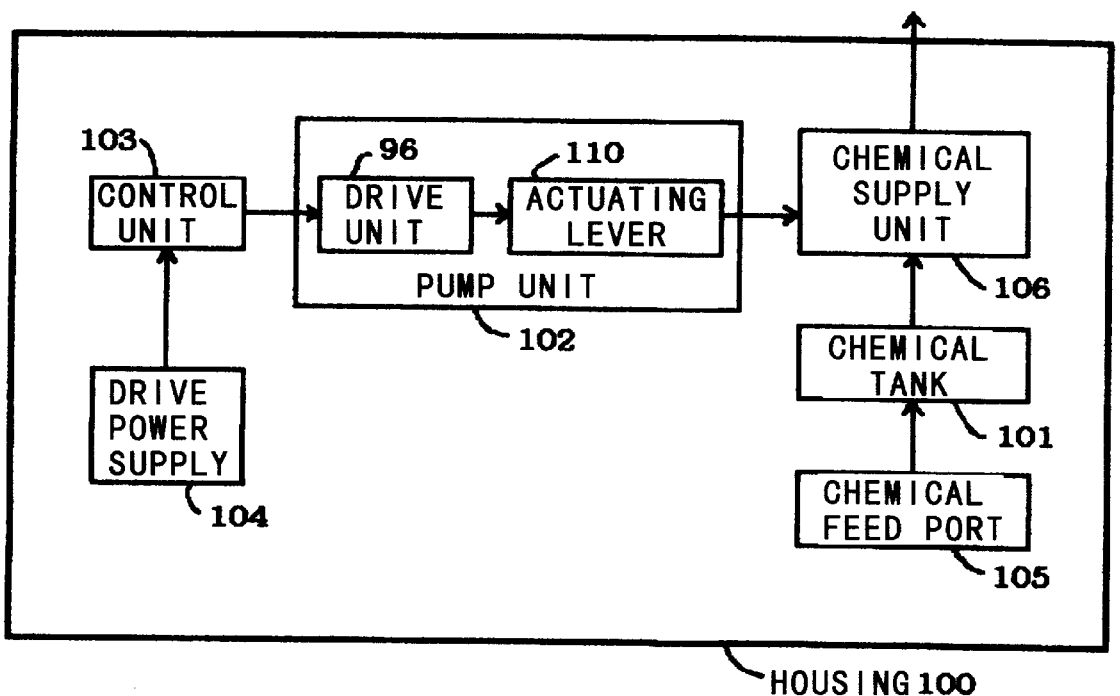
FIG. 1 is a block diagram showing the entire structure of an implant-type chemical supply device according to the present invention.

FIG. 1 is a block diagram showing an implant-type chemical supply device according to an embodiment of the present invention. Generally, within a housing 100 of the device implanted in a body are disposed a chemical tank 101, a pump unit 102, and control unit 103, and a drive power supply (battery) 104.

Chemicals is fed to the chemical tank 101 from a chemical feed port, and then supply to an affected part by chemical supply unit (supply tube) 106.

The pump unit 102 is a drive source for supplying the chemicals due to the chemical supply unit 106 and made up of drive unit (step motor) 96 and an actuating lever 110 driven by the drive unit (step motor) 96. The drive unit (step motor) 96 is rotationally driven under the control by the control unit 103 and operated by a power supplied from the battery (power supply) 104.

Figure 2:
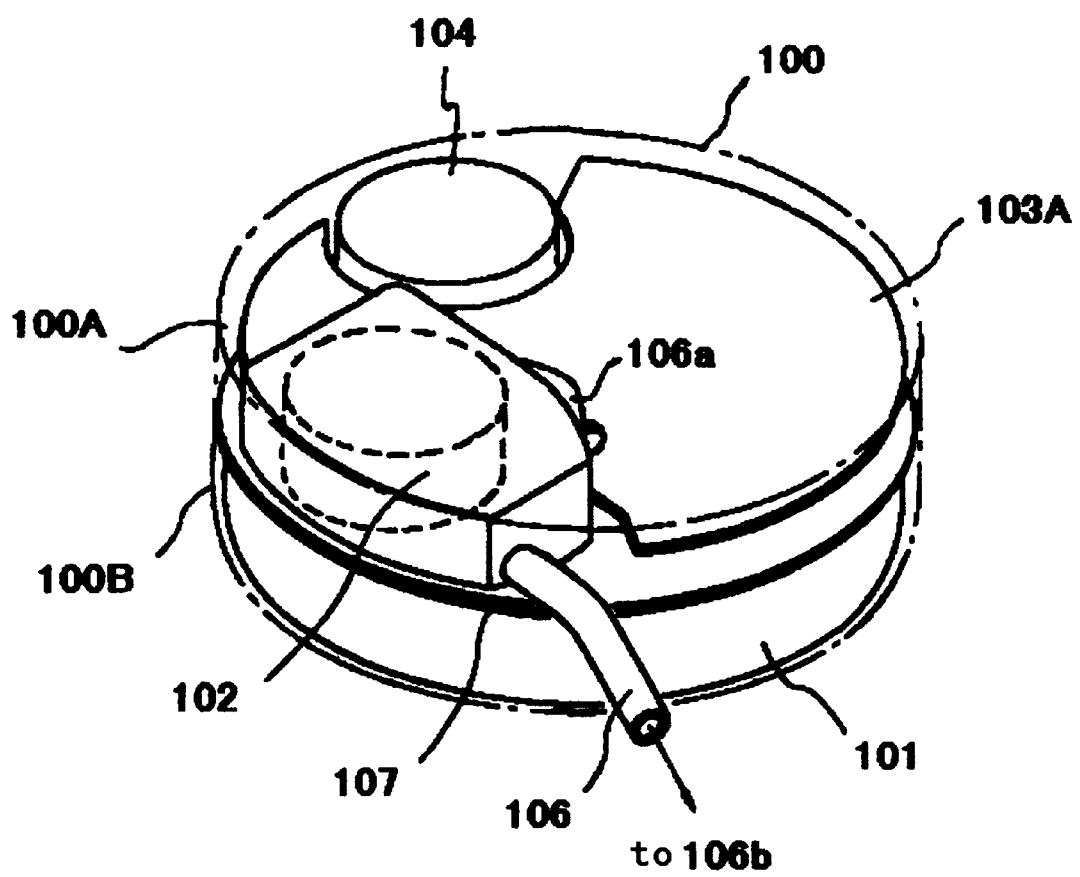
FIG. 2 is a perspective view showing an appearance of the implant-type chemical supply device shown in FIG. 1.

FIG. 2 is a perspective view showing the internal structure of the housing 100.

The housing 100 is substantially disc-shaped and of a two-divided structure consisting of an upper case 100A and a lower case 100B. A chemical tank 101 for storing a predetermined amount of chemicals is disposed within the lower case 100B and filled with the predetermined amount of chemicals. The chemical tank 101 connects to one end 106a of the supply tube 106 the other end 106b of which is led up to a position of the affected part outside of the housing 100.

Within the upper case 100A are disposed the pump unit 102, a circuit board 103A that constitutes the control unit 103, and the battery 104. A partition 107 is arranged between those upper case 100A and lower case 100B.

Figure 3:
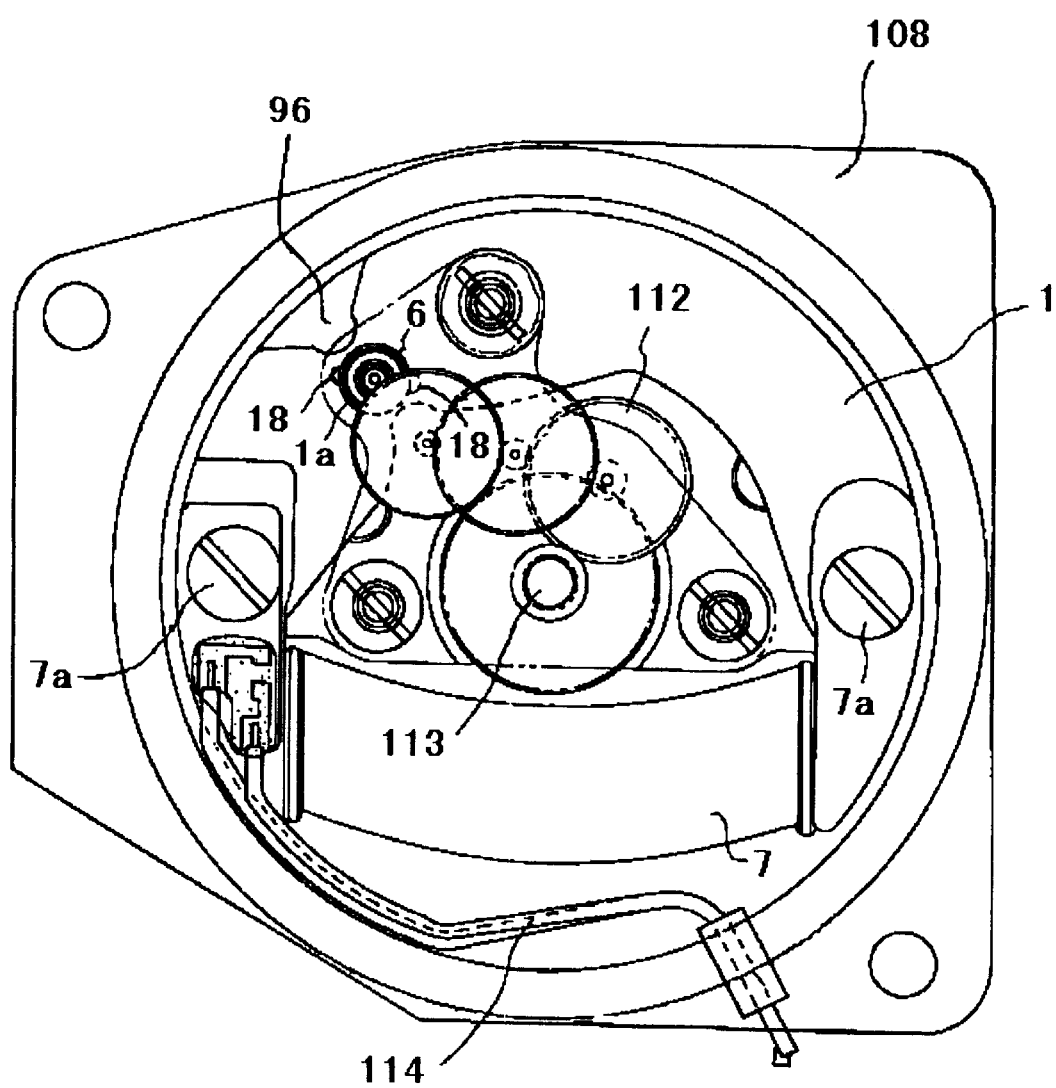
FIG. 3 is a front view showing an internal structure of the implant-type chemical supply device shown in FIG. 1.
Figure 4:
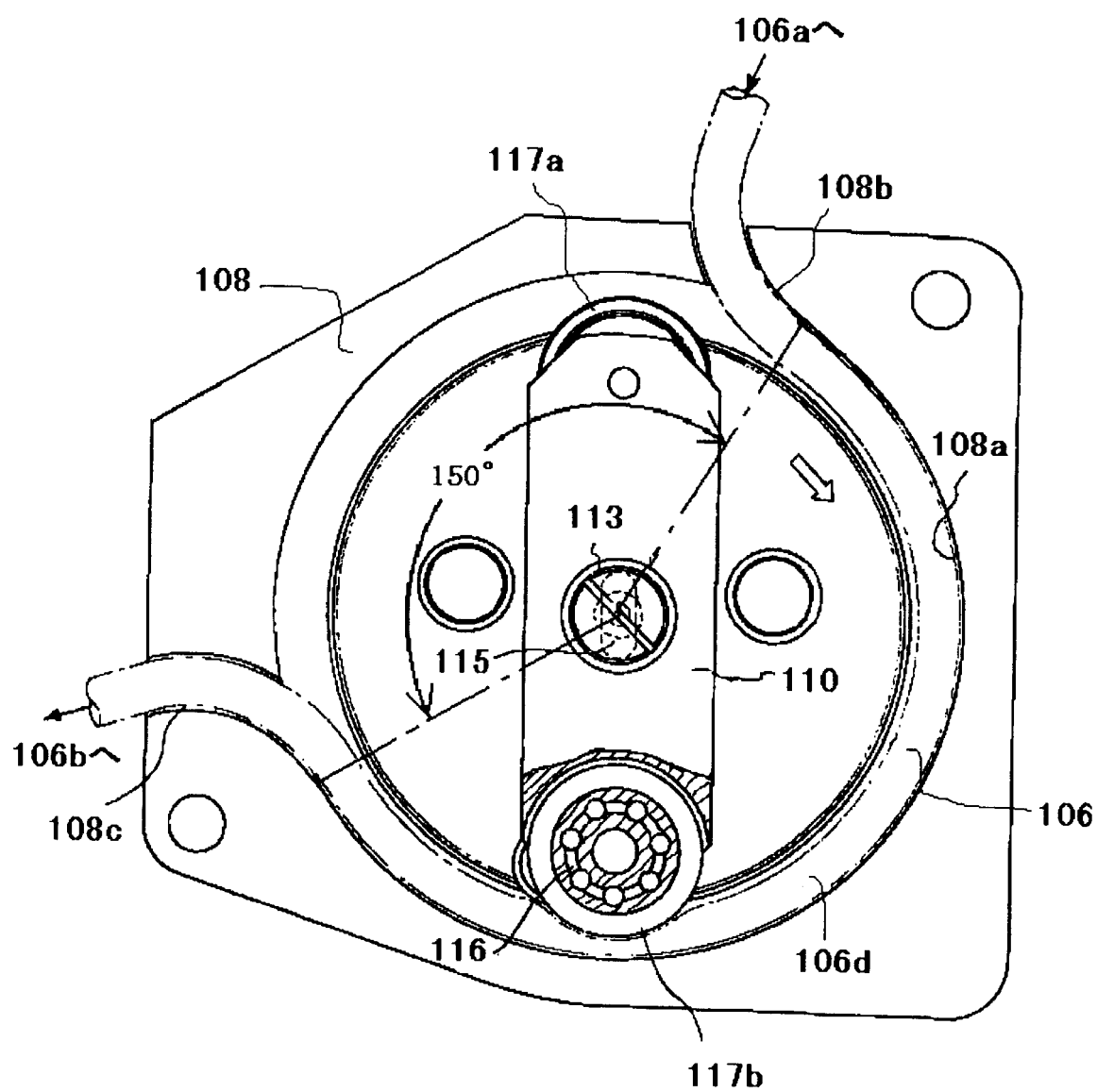
FIG. 4 is a back view showing an internal structure of the implant-type chemical supply device shown in FIG. 1.
Figure 5:
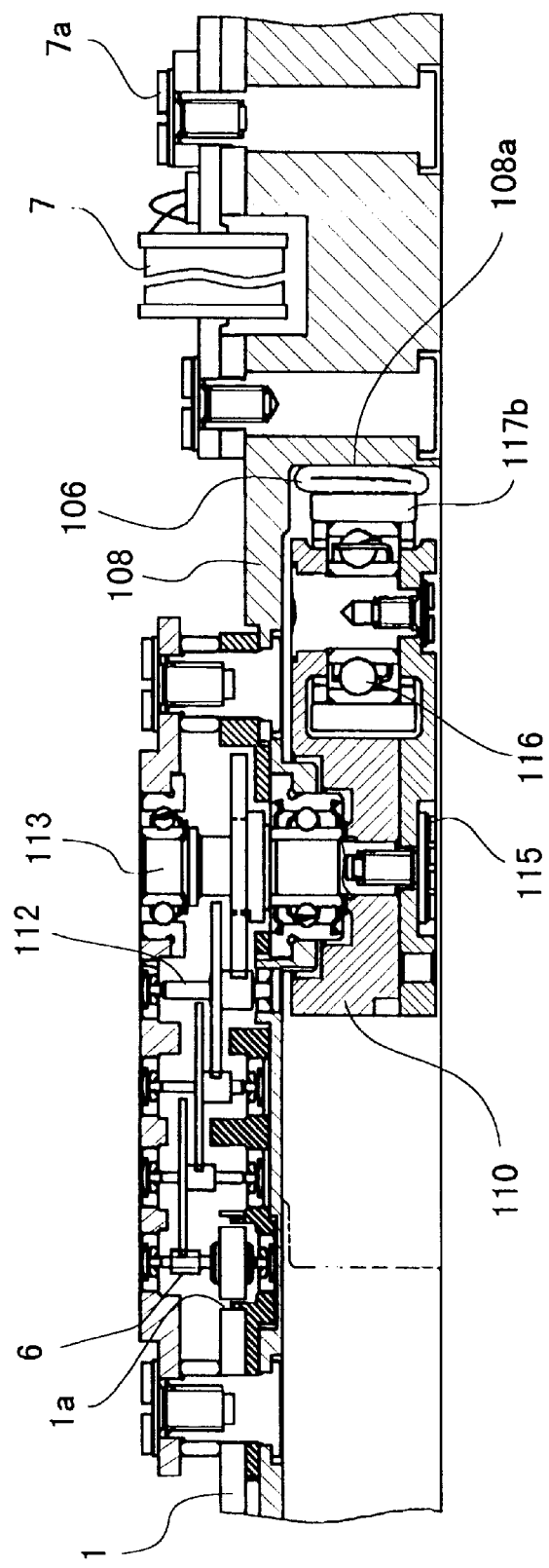
FIG. 5 is a cross-sectional view showing an internal structure of the implant-type chemical supply device shown in FIG. 1.

FIG. 3 is a front view showing the internal structure of the pump unit 102, FIG. 4 is a back view thereof, and FIG. 5 is a cross-sectional view thereof.

The structural portion of the step motor 96 is integrated into a front side of a support 108 of the pump unit 102, and the respective structures of the chemical supply unit 106 are integrated into a back side thereof. As shown in FIG. 3, the step motor 96 is of an integrated stator, and a stator 1 is magnetically coupled with a coil 7 through set screws 7a. A notch 18 is fitted to an inner hole 1a of the stator 1 for determining the rotating direction of the rotor 6 which is magnetized to two poles in a radial direction thereof.

The rotor 6 is coupled to a rotating shaft 113 that penetrates the center of the pump unit 102 through a wheel train 112 consisting of a plurality of gears at a predetermined gear ratio. Both ends of the coil 7 are connected to the control unit 103 through a conductive lead wire 114 so that a required power is supplied to the coil 7 from the battery 104.

As shown in FIG. 4, an inner wall surface 108a, and tube guide grooves 108b, 108c are formed on the back side of the support 108 so as to be substantially U-shaped with the rotating shaft 113 as its center. A part 106d of the supply tube 106 is disposed in the form of an arc along the inner wall surface 108a.

The central portion of the actuating lever 110 is fixed to the rotating shaft 113 with a set screw 115, and both ends of the actuating lever 110 are provided with rotatable rollers 117*a* and 117*b* having rotating shaft bearings 116 therein, respectively.

Those rollers 117*a* and 117*b* are disposed so as to be in contact with the inner peripheral surface of the arcuate supply tube 106*d* under a given pressure, respectively.

With the above structure, upon the rotation of the rotor 6 by the drive of the step motor 96, the rotating shaft 113 and the actuating lever 110 are rotated through the wheel train 112, and the rollers 117*a* and 11*b* gradually extrude the chemicals within a part 106*d* of the supply tube 106 in the rotating direction and supplies the chemicals to the affected part.

Figure 6:
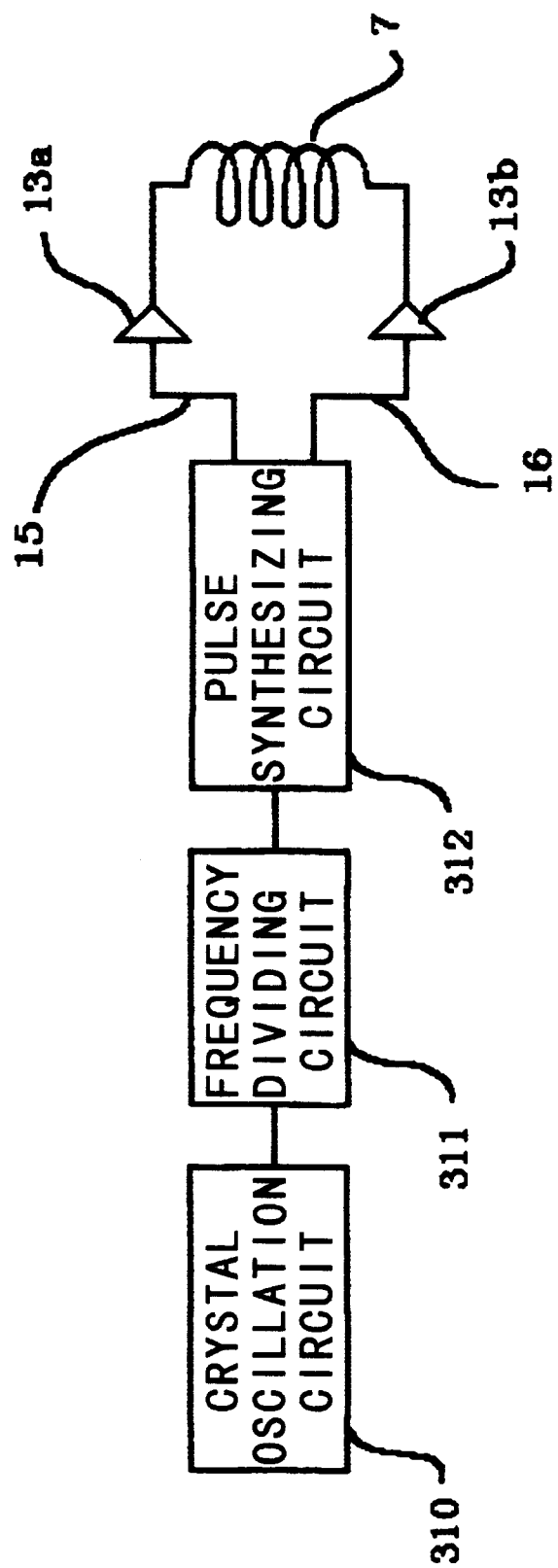
FIG. 6 is a circuit diagram showing a structural example of a basic circuit of a pump unit.

FIG. 6 is a diagram showing the drive circuit of the step motor 96.

Figure 7:
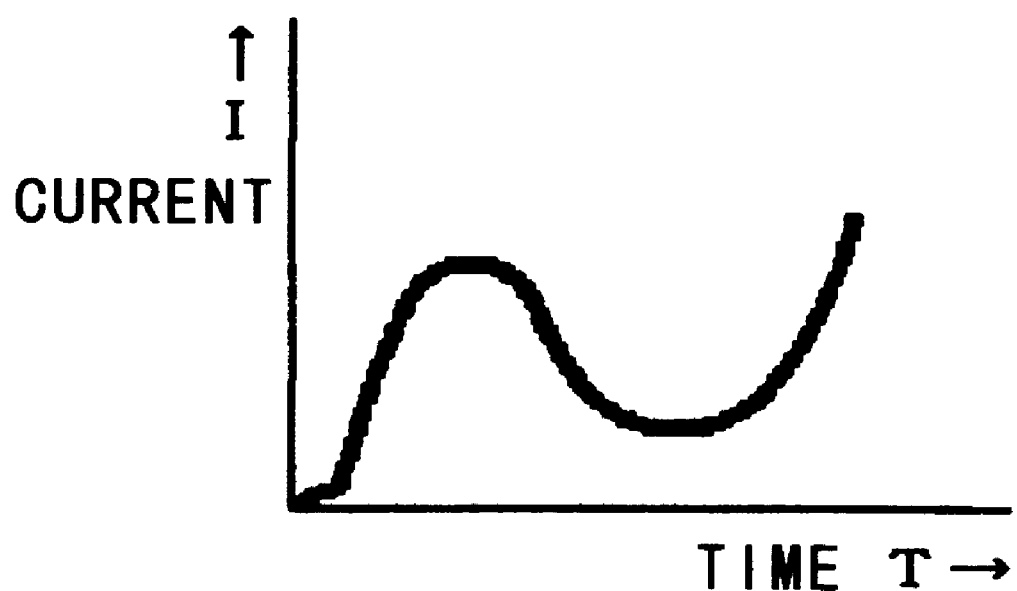
FIG. 7 is a diagram showing one example of a drive current waveform of a step motor.

An oscillation signal from a crystal oscillation circuit 310 is sequentially frequency-divided by a frequency dividing circuit 311. Each of those dividing signals is converted by a pulse synthesizing circuit 312 into two signals which are, for example, 10 msec in pulse width, 62.5 msec in period and 31.25 msec in phase difference, and then supplied to input terminals 15 and 16 of drive invertors 13*a* and 13*b*, as a result of which inversion pulses of a current whose flowing direction is changed every 31.25 msec are supplied to the coil 7, and the rotor 6 magnetized to two polarities is sequentially rotated every 180 degrees. An example of a coil current waveform when the rotor 6 is normally driven is shown in FIG. 7.

Then, a principle of the rotational position detecting operation of the rotor 6 in the step motor 96 will be described.

As a method of detecting the rotational position of the rotor 6, there are proposed a method in which the position is detected by a mechanical switch or an external element such as hole element, however, it is very difficult to equip those mechanisms within a very small volume such as the implant-type chemical supply device.

In the present invention, a detecting circuit can be equipped in the same integrated circuit together with the oscillating, frequency-dividing and drive circuits, etc., without any provision of an external element. As one example of a method of detecting the rotational position of the rotor 6, two kinds of different detecting principles will be described.

A first method is to employ that a drive current waveform is different depending on the position of the rotor 6 in the case where the integrated stator is used.

Figure 8:
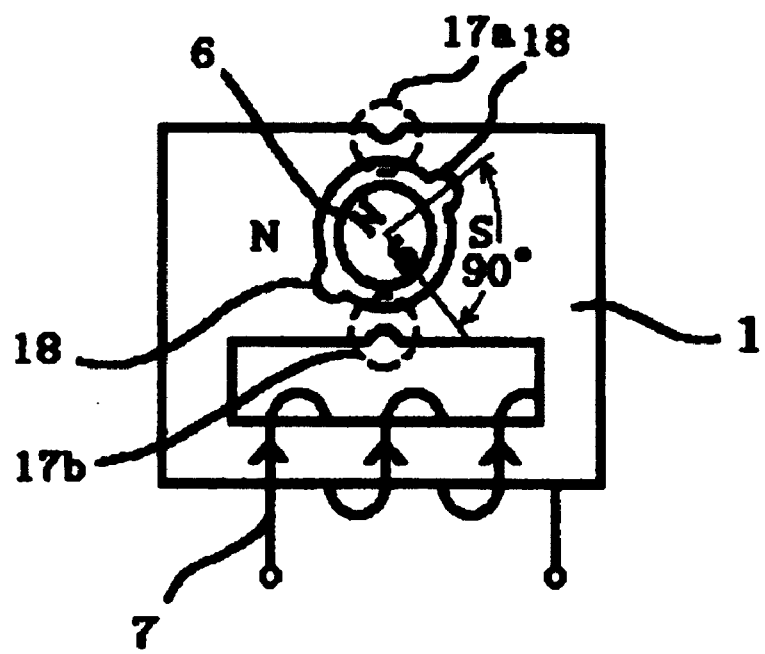
FIG. 8 is an explanatory diagram showing one principle of the detection of a rotational position of a rotor.

FIG. 8 shows a state immediately after a current is supplied to the coil 7, in which when the current is not supplied to the coil 7, the rotor 6 gets stationary at a position where angle defined by the notch 18 and the rotor magnetic pole is nearly 90 degrees. In this state, when the current flows into the coil 7 in a direction indicated by an arrow, magnetic poles are developed in the stator 1 as shown in FIG. 8, and the rotor 6 is made repulsive and rotated clockwise. When the current flowing into the coil 7 is discontinuous, the rotor 6 gets still in a state where the magnetic poles are inverse to that shown in FIG. 8. Thereafter, a current is made to flow into a direction opposite to the coil 7, whereby the coil 6 sequentially continues to rotate clockwise.

The step motor 96 made up of the integrated stator having a supersaturation portion 17 as described above, a current waveform when the current is made to flow into the coil 7 has a gentle rising portion as shown in FIG. 7. This is because a magnetic resistance of the magnetic circuit viewed from the coil 7 is very low until the supersaturation portion 17 of the stator 1 is saturated with the result that the time constant γ of a series circuit consisting of a resistor and a coil is increased. This is represented by the following expression.

$$\gamma = L/R \quad L \approx N^2/Rm$$

Therefore $\gamma \acute{E} = N^2/(R \times Rm)$ where L is an inductance of the coil 7, N is the number of turns of the coil 7 and Rm is a magnetic resistance.

When the supersaturation portions 17*a* and 17*b* of the stator 1 are saturated, since the magnetic permeability of the saturated portion is identical with that of air, Rm is increased, and the time constant γ of the circuit is reduced. As a result, as shown in FIG. 7, the current waveform rapidly rises. Also, since the saturation period of time is also influenced by the magnetic state of the motor, the saturation period of time gets elongated more as the current level when the pulse is interrupted becomes higher. Therefore, since the saturation period of time becomes good after a corrected drive pulse is supplied to the step motor 96, it is preferable that the demagnetization pulse for canceling that effect is supplied to the step motor 96. In the operation detection of the rotor 6 according to this example, a difference in time constant of the above series circuit consisting of the resistor and the coil after drive is made by a normal pulse is taken.

Subsequently, a reason why a difference in time constant is exhibited will be described with reference to the drawings.

Figure 9:
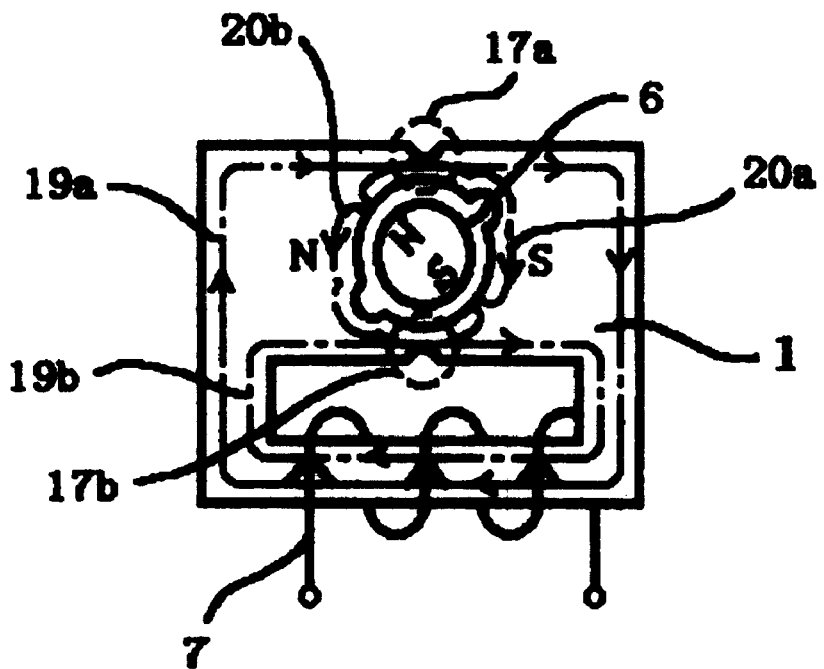
FIG. 9 is an explanatory diagram showing one principle of the detection of a rotational position of a rotor.

FIG. 9 shows an appearance of a magnetic field when the current starts to be made to flow into the coil 7, in which the rotor 6 provides magnetic poles at a rotatable position. The lines of magnetic flux 20*a* and 20*b* represent the appearance of the magnetic flux developed from the rotor 6, and although in fact, the magnetic flux interlinked with the coil 7 also exists, it is omitted here. The lines of magnetic flux 20*a* and 20*b* represent the saturation portions 17*a* and 17*b* of the stator 1 which are directed as indicated by an arrow in FIG. 9. The supersaturation portions 17*a* and 17*b* are not yet saturated in the most cases. In this state, the current is made to flow into the coil 7 as indicated by the arrow so that the rotor 6 is rotated clockwise. Because the magnetic flux 19*a* and 19*b* developed by the coil 7 and the magnetic flux 20*a* and 20*b* developed from the rotor 6 intensify each other at the supersaturation portions 17*a* and 17*b* of the stator 1, the supersaturation portions 17*a* and 17*b* of the stator 1 are smoothly saturated.

Figure 11:
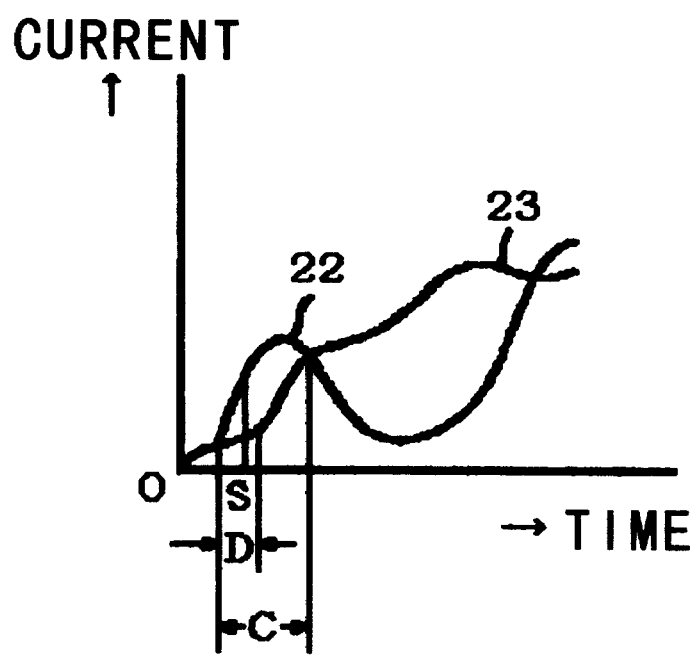
FIG. 11 is a diagram showing one example of a drive current waveform of the step motor.

Thereafter, a magnetic flux sufficient for rotating the rotor 6 is developed in the rotor 6, but it is omitted from FIG. 9. The waveform of a current that flows into the coil is indicated by reference numeral 22 of FIG. 11.

Figure 10:
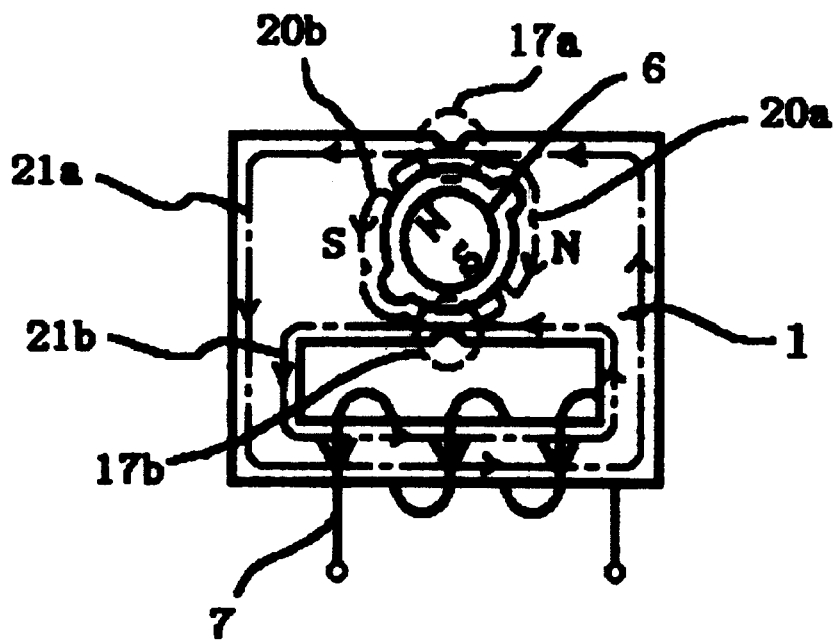
FIG. 10 is an explanatory diagram showing one principle of the detection of a rotational position of a rotor.

On the other hand, FIG. 10 shows a state of the magnetic flux when the current is made to flow in the coil 7 in a situation where the rotor 6 is returned without being rotatable for some reason. Naturally, in order to rotate the rotor 6, the current must be made to flow into the coil 7 in a direction opposite to the arrow, that is, in the same direction as that of FIG. 9. However, since an inversion current whose current direction is changed every one time is supplied to the coil 7, such a state is caused when the rotor 6 cannot be rotated.

Since the rotor 6 cannot be rotated, the direction of magnetic flux generated from the rotor 6 is identical with that of FIG. 9. Since the current flows into the coil 7 in the direction opposite to that of FIG. 9, the directions of magnetic flux become directions indicated by 21*a* and 21*b*. In the supersaturation portions 17*a* and 17*b* of the stator 1 the magnetic flux developed by the rotor 6 and the coil 7 is canceled by each other, and in order to saturate the supersaturation portion of the stator 1, a longer period of time is required. This state is indicated by reference numeral 23 in FIG. 11.

Figure 12:
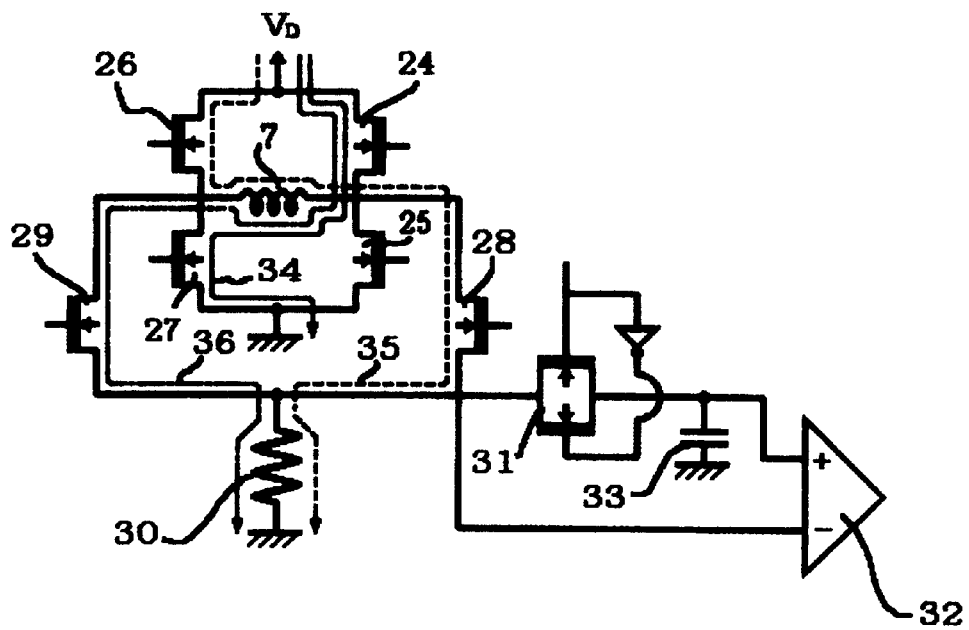
FIG. 12 is a diagram showing one example of an operation detecting circuit of the rotor.

An example of the rotational position detecting circuit of the rotor 6 using the above phenomenon is shown in FIGS. 12 and 13. FIG. 12 shows a position detecting circuit of the rotor 6 which is made up of detection gates 28, 29, a detection resistor 30, a transmission gate 31 for charging a capacitor, a capacitor 33 and a voltage comparator 32 being added to MOS gates 24, 25, 26 and 27 that constitute a conventional drive circuit, that is, the drive invertor.

First, an example of normal drive will be described. A current is made to flow into the coil 7 through a path 34 so that the coil 7 is excited to drive the rotor 6. After the motion of the rotor 6 is nearly completed, a first detection pulse is supplied to the coil 7 through a path 35 for a short period of time (about 30 msec to 1 msec), and thereafter a second detection pulse is supplied to the coil 7 through a path 36.

Assuming that the rotor 6 is normally rotated by one step by the normal drive pulse, when the first detection pulse is applied to the coil 7, a relation between the rotor magnetic pole and the stator magnetic pole is such that the rotor 6 can be again driven by one step as shown in FIG. 9. The rising portion of the current waveform at this time exhibits a waveform having an early rising as indicated by reference numeral 22 of FIG. 11. Then, when the second detection pulse is applied to the coil 7, since the position of the rotor 6 is identical with that in case of the first detection pulse (since the pulse width of the detection pulse is short, and a high resistor 30 is connected in series to the coil 7, the rotor 6 is not rotated by the detection pulse), and the direction of excitation is opposite to that in case of the first detection pulse, the relation between the rotor magnetic pole and the stator magnetic pole is represented as shown in FIG. 10, in which the rising portion of the current waveform becomes a waveform having a late rising as indicated by reference numeral 23 of FIG. 11. Since the detection resistor 30 is connected in series to the coil at the time of application of the detection pulse, it is not identical with the waveform of FIG. 11 in the strict sense, but the feature of the rising portion is not changed.

Figure 13A:
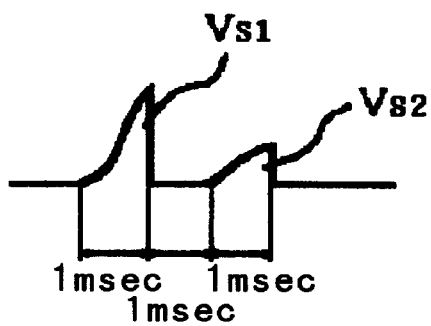
FIG. 13 is a diagram showing an example of a detection voltage waveform of the circuit shown in FIG. 12.

When the terminal potential of the detection resistor 30 is observed, a potential Vs1 due to the first detection pulse rises up to a higher potential than a potential Vs2 due to the second detection pulse, as shown in FIG. 13A.

Figure 13B:

Then, in the case where the rotor 6 is returned to an initial position without being rotatable by one step by the normal drive pulse, the relation between the rotor magnetic pole and the stator magnetic pole at the time of application of the first and second detection pulses is reverse to that at the time of the above normal rotation with the result that the terminal potential of the detection resistor 30 satisfies Vs1<Vs2 as shown in FIG. 13B.

Accordingly, by comparing the magnitude of Vs1 with that of Vs2, the operation detection of whether or not the rotor 6 operates normally by the normal drive pulse is performed. According to an experiment, a potential difference between Vs1 and Vs1 was about 0.4 V. If the difference is this degree, the detection is easily enabled. For example, in the structure shown in FIG. 12, the timing gate 31 of the first detection pulse is made in an on-state so that the capacitor 33 is charged by Vs1, and then the potential Vs1 charged in the capacitor 33 and the terminal potential Vs2 of the detection resistor 30 may be compared by the voltage comparator 33 at the application of the second detection pulse.

The description of the first method for the rotational position detection of the rotor 6 is completed, and then a description will be given of an principle in which the rotational position detection of the rotor 6 is conducted from a voltage waveform induced in the coil by the free oscillation of the rotor 6 after the rotor 6 is driven.

Figure 14A:
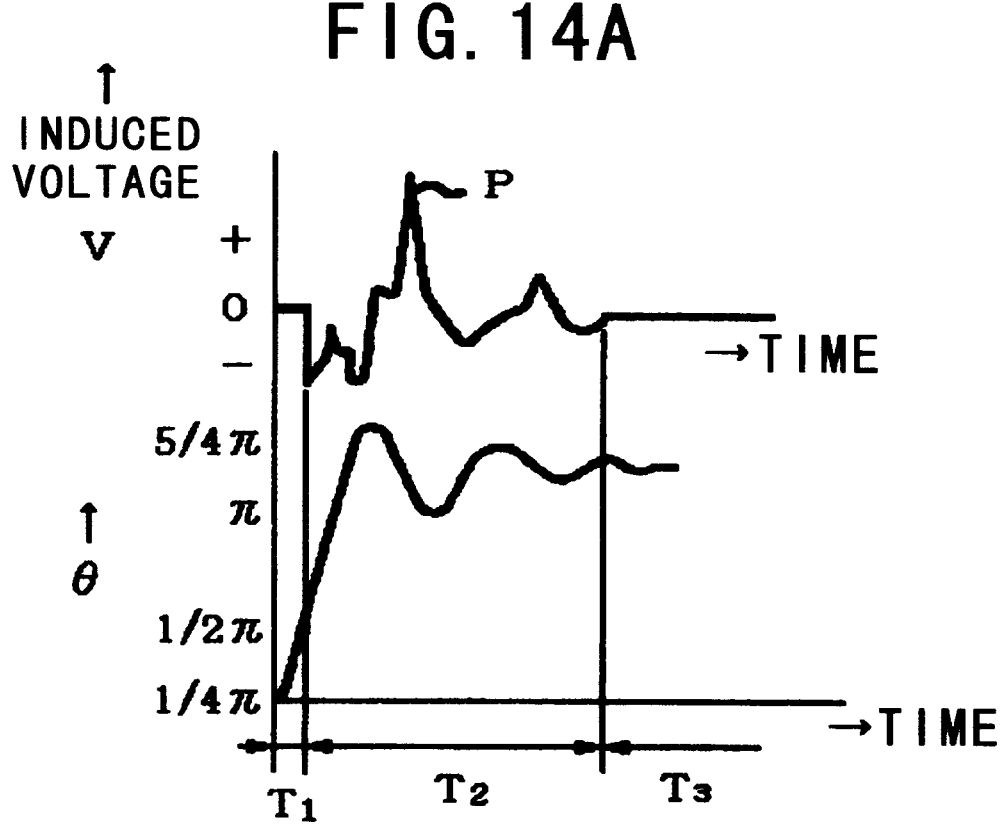
FIGS. 14A and 14B are diagrams showing an rotating angle and an induced voltage of the rotor after the rotor is driven, respectively.
Figure 14B:
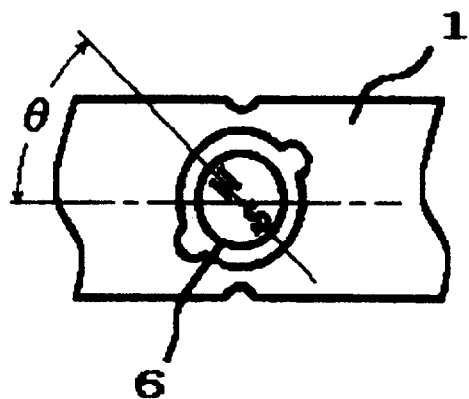

FIG. 14A shows the induced voltage waveform of the coil which is developed on both ends of the high resistor and the rotating angle of the rotor 6 when both ends of the coil is connected to the high resistor of several tens k$\Omega$ after a normal drive pulse is applied to the coil, where $\theta$ represents an angle between the stator parallel shaft and the magnetic pole as shown in FIG. 14B.

A section T1 is a section where the drive pulse is applied to the coil, and since the above high resistor (detection resistor) is not connected to the circuit, no induced voltage waveform is exhibited. A subsequent section T2 is a voltage induced in the coil by the interlocking of rotation and oscillation of the rotor 6 after the drive is completed. Since the voltage waveform in the section T2 is changed according to the load state and the drive conditions of the step motor 96, the rotational position of the step motor 96 can be detected by detection of a change in the voltage waveform.

Figure 15:
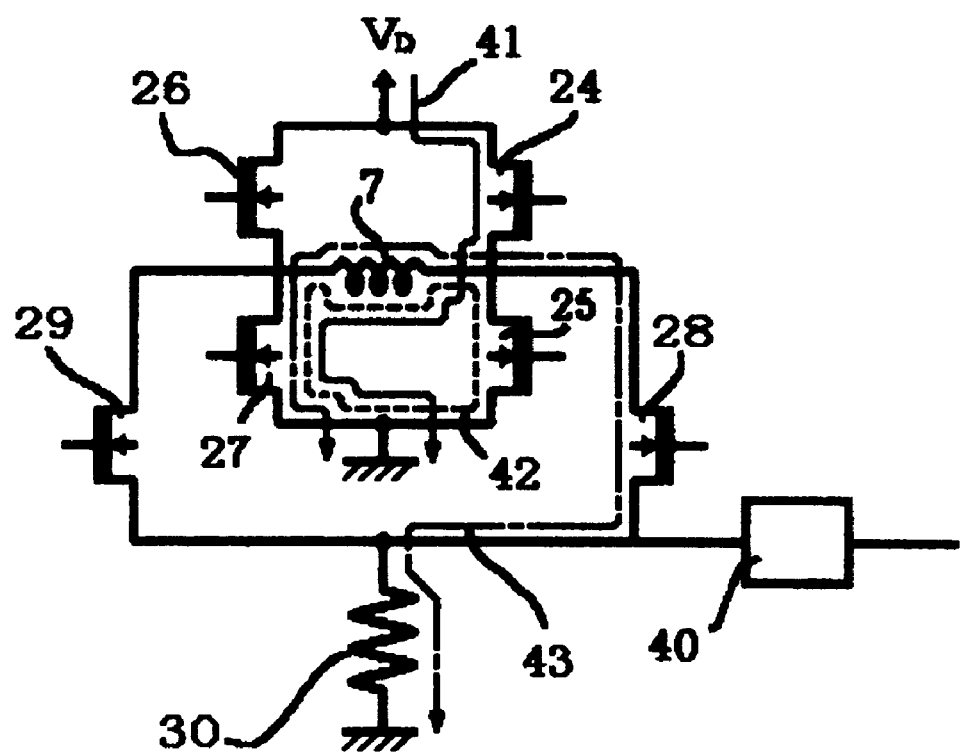
FIG. 15 is a diagram showing one example of the operation detecting circuit of the rotation according to another principle.

FIG. 15 shows an example of the detecting circuit according to this principle. The gates 24 to 29, the detection resistor 30 and the coil 7 are different only in input signal from that shown in FIG. 12 and completely identical with those of FIG. 12. A node of the detection resistor 30 is connected to an input terminal of the voltage detector 40 having a predetermined threshold value. When the coil is excited in the path 41 by the normal drive pulse, the rotor 6 is then driven.

Thereafter, a state in which both ends of the coil 7 are grounded to be short-circuited through the path 42 during the motion of the rotor 6, and a state in which a closed loop including the high-resistance detection resistor 30 is formed by the path 43 are discontinuously changed over. The effect obtained by discontinuously changing over those states will be described later, and the state in which the closed loop including the detection resistor 30 is formed immediately after the rotor 6 is driven will be first described.

Figure 16A:
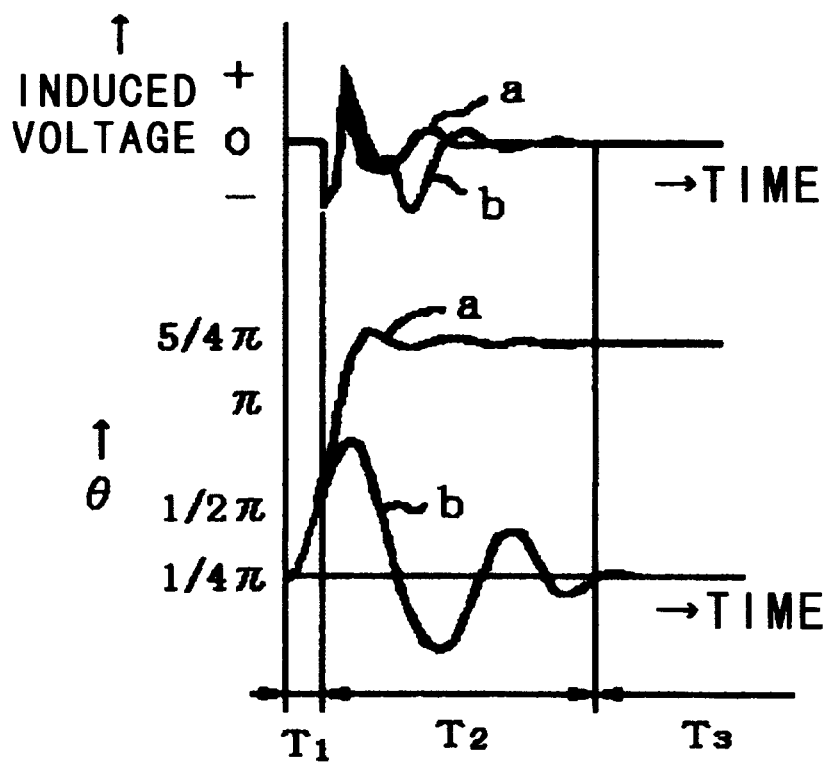
FIGS. 16A and 16B are diagrams showing an rotating angle and an induced voltage of the rotor after the rotor is driven, respectively.
Figure 16B:
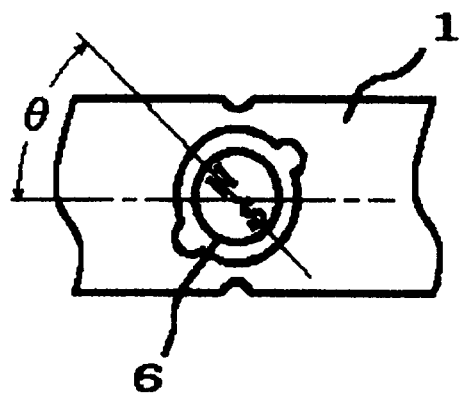

FIG. 14 is the waveform of the terminal potential of the detection resistor 30 in that state. The step motor 96 of FIG. 14 is in a substantially non-load state. In FIG. 16A, the induced voltage waveforms and the rotating angle at the time of the maximum load and at the time of overload are indicated by marks a and b. $\theta$ is an angle between the stator parallel shaft and the magnetic pole as shown in FIG. 16B.

At the time of the maximum load a, because the rotation of the rotor 6 is slow and the oscillation after the rotor is rotated by one step is also small at the time of the maximum load a, the induced voltage becomes a waveform reduced in undulations. Also, at the time of overload b, the undulations of the induced voltage waveform is reduced except that a large peak voltage is induced in a negative direction when the rotor 6 is returned to the initial position.

There are proposed various methods by which the rotation/non-rotation of the rotor 6 is judged from the induced voltage waveform. However, a method of judging the presence/absence of a peak P shown in FIG. 14 is simple and stable from the viewpoint of the circuit. That is, the rotation/non-rotation of the rotor 6 is judged according to whether the terminal voltage of the detection resistor 30 reaches a predetermined potential or more, or not, within a given period of time where the peak P is considered to be generated several msec after the application of the normal drive pulse to the coil is completed.

In this method, as shown in FIG. 16A, the rotation at the time of the maximum load is regarded as non-rotation.

However, in the case where the above detection principle is applied to the correction drive system, etc., as in the present invention, it is an error in view of safety, and since the correction drive pulses in the same direction are too outputted, there is no case in which the rotor 6 is too rotated.

Figure 17:
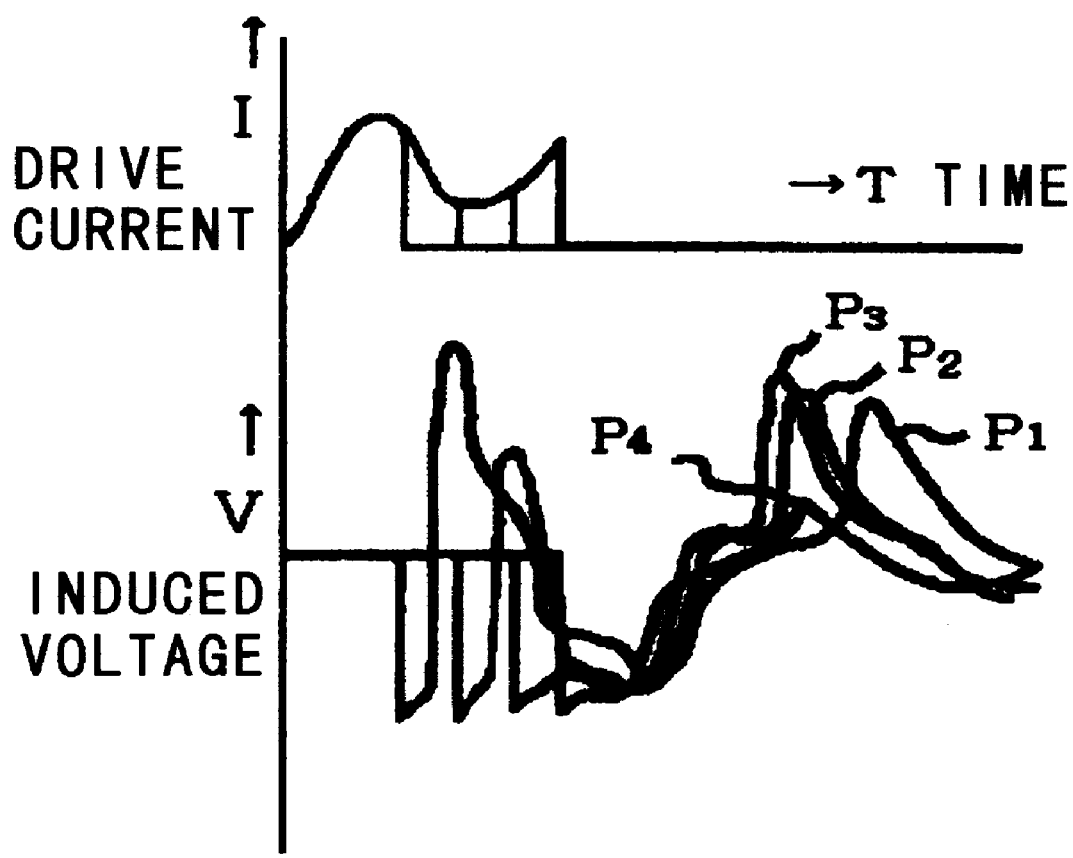
FIG. 17 is a diagram showing a current waveform and an induced voltage waveform when a drive pulse width is variously changed.

FIG. 17 shows a coil induced voltage waveform after the rotor is driven when the pulse width of the normal drive pulse is variously changed.

As is understood from this figure, when the pulse width of the normal drive pulse becomes long to a certain degree, the height of the peak P of the induced voltage waveform becomes low regardless of the non-load and the normal rotation. For facilitation of understanding, FIG. 18 takes the pulse width of the normal drive pulse as the axis of abscissa and the potential of the peak P of the induced voltage as the axis of ordinate. Reference numeral 45 represents a case in which the detection resistor is continuously connected in series to the coil after the drive is made as described above to form the closed loop, and reference numeral 46 represents a case in which the detection resistor is discontinuously connected within the closed loop as will be described below.

The effects obtained by connecting the high-resistance detection resistor within the closed loop discontinuously including the coil after the normal drive pulse is applied will be described below. Because the drive circuit is driven by two invertors as shown in FIG. 6, both ends of the coil of the motor are short-circuited by the low resistance within the driver which forms the invertor at the time of non-driving, and the current flowing in the coil by the induced voltage is made to flow in the short-circuit of the coil path 42 shown in FIG. 15, and that current is consumed by the resistance transistor for the driver as the Joule heat, to thereby brake the rotor 6.

Also, in order to detect the induced voltage, in the case where the closed loop is formed by the path 43 of FIG. 5, the high-resistance detection resistance 30 is connected in series other than the driver circuit, and therefore the current of the brake circuit becomes smaller than the former.

When the rotor 6 is braked, both of those circuits are switched with the result that a rapid current change is caused in the circuit. However, because the coil of the motor is large in inductance, it cannot follow a change in that current, and exhibits a response with a first-order lag which is the time constant $\gamma=L/Rd$ due to the resistor Rd (=R+R30) of the brake circuit and the inductance L of the coil.

Figure 19:
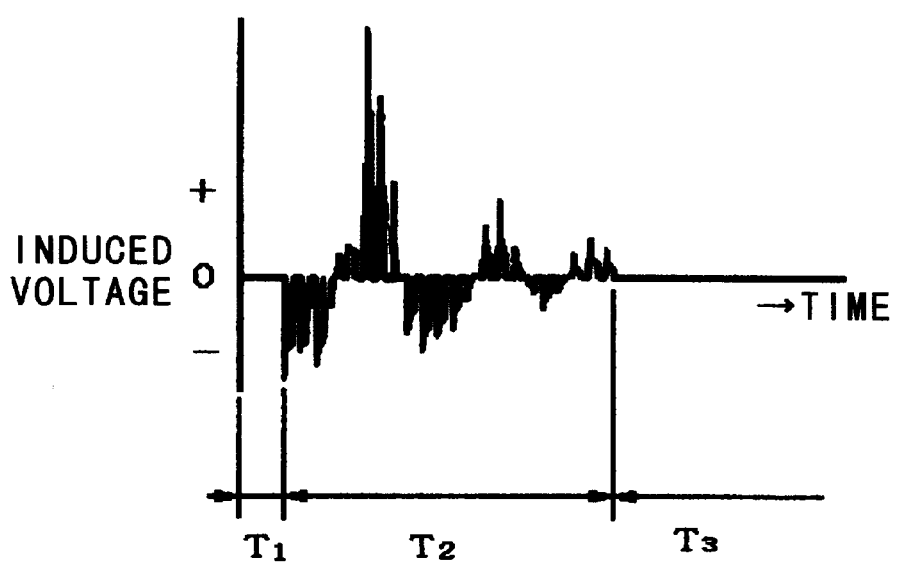
FIG. 19 is a diagram showing one example of the operation detection induced voltage waveform of the rotor.

The voltage developed at both ends of the detection resistor 30 (R30) is zero V at the time of the brake circuit by the path 42 in FIG. 15, and because the coil 7 allows the current at the time of braking to continuously flow by the path 42 as it is immediately when the path 42 is changed to the path 43, a high voltage is instantaneously developed on both ends of the detection resistor 30 which is relatively high resistance, and thereafter the high voltage is attenuated by the above time constant $\gamma$. An example of the terminal voltage of the detection resistor 30 at that time is shown in FIG. 19.

Figure 18:
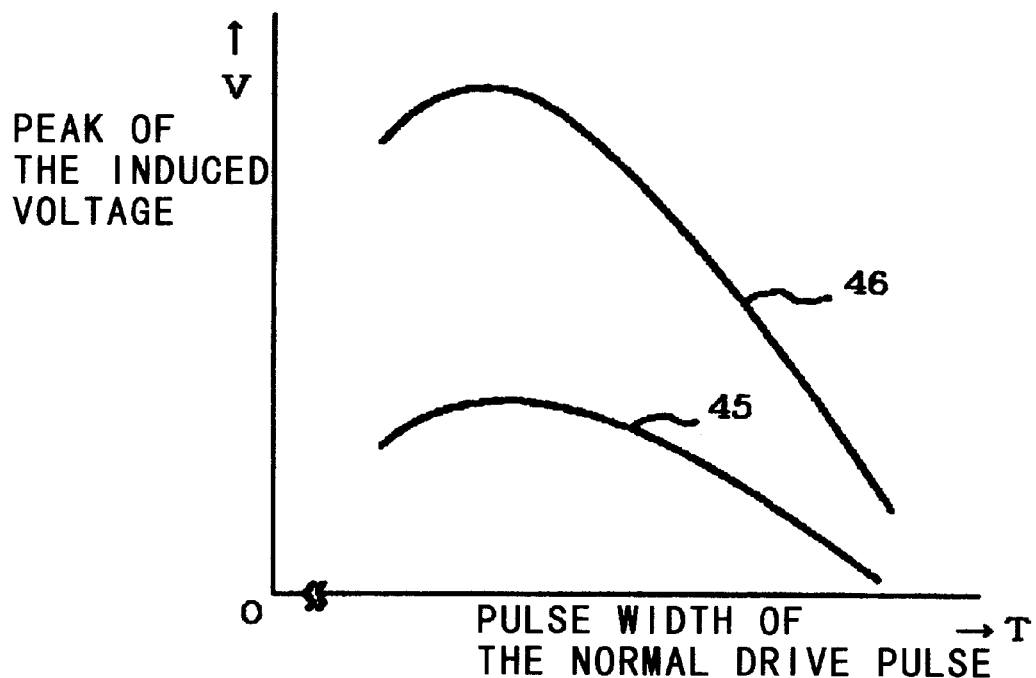
FIG. 18 is a graph showing a relation between the drive pulse width and a peak potential of the subsequent induced voltage.

The feature of this system is that the voltage induced by the motor at the time of braking can be amplified by only changing over the resistant value of the circuit that performs the rotor brake, and the maximum value of the high voltage of the peak voltage in the case of continuously detecting the induced voltage as indicated by reference numeral 45 of FIG. 18 is about 0.8 V, whereas in the case the detection resistance is discontinuously connected as indicated by reference numeral 46, the maximum value reaches equal to or more than the supply voltage of drive circuit (about 3 V). Accordingly, it is very easy to detect such a voltage. By the way, as is apparent from FIG. 18, when the pulse width of the normal drive pulse reaches a certain value or more, there occurs a phenomenon where the undulations of the inducted voltage become small. Therefore, attention must be paid to that phenomenon.

The principle of the two kinds of the rotor operation detecting circuit was described above. The subject matter of the present invention is that the normal drive pulse width is increased and decreased, and although the structure of the step motor 96 and the operation detecting circuit of the step motor 96 are important elements, the present invention is not limited by or to the above description.

Subsequently, a main portion of the embodiment according to the present invention will be described.

Figure 20:
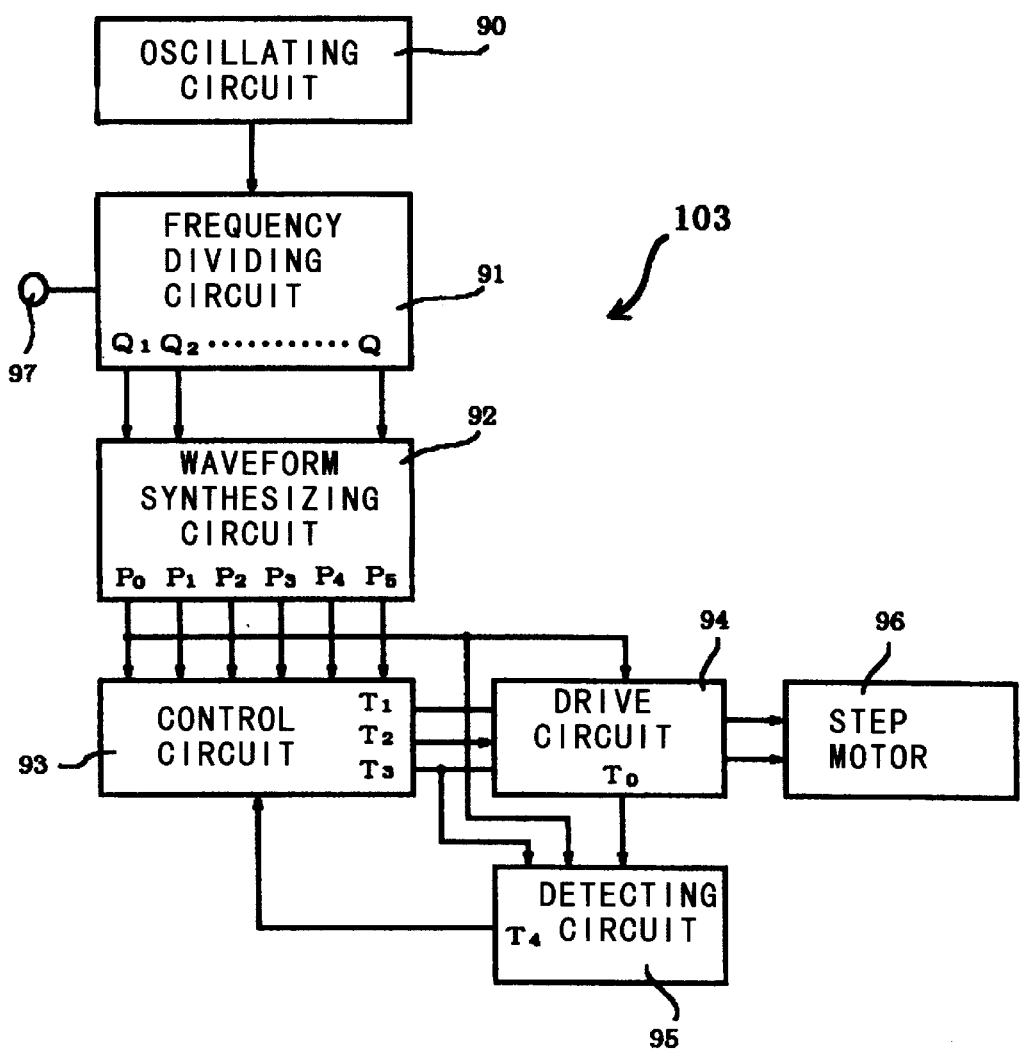
FIG. 20 is a block diagram showing one embodiment of the present invention.

FIG. 20 is a block diagram showing the structure of the control unit 103. Reference numeral 90 denotes an oscillating circuit for which a crystal oscillator that normally oscillates at 32768 Hz is used. Reference numeral 91 denotes a frequency dividing circuit which divides the frequency at a stage of a flip flop circuit 10 to obtain a timing 31.25 msec in case of the above oscillation frequency. Reference numeral 97 denotes a reset input, and upon resetting, the dividing stage is all reset.

Figure 21:
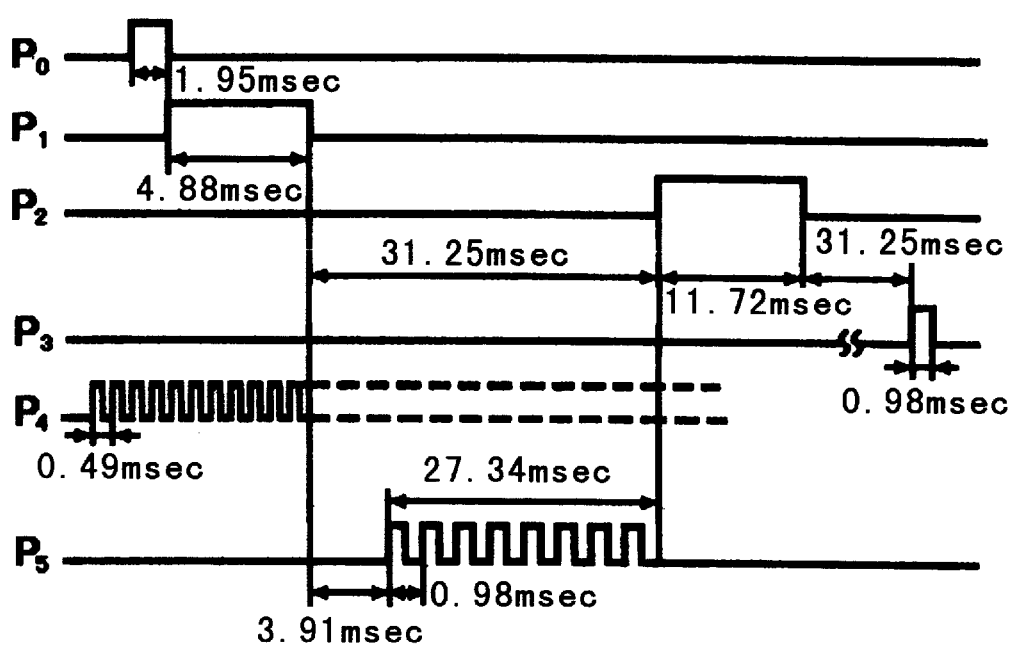
FIG. 21 is a timing chart showing pulses necessary for the present invention.

Reference numeral 92 is a waveform synthesizing circuit, in which a desired pulse from the output of the flip flop circuit obtained by the dividing circuit 91 is waveform-synthesized by a NAND gate, a NOR gate or the like as shown in a timing chart of FIG. 21. Because this synthesis enables the circuit design logically and readily, the circuit diagram will be omitted.

Figure 22:
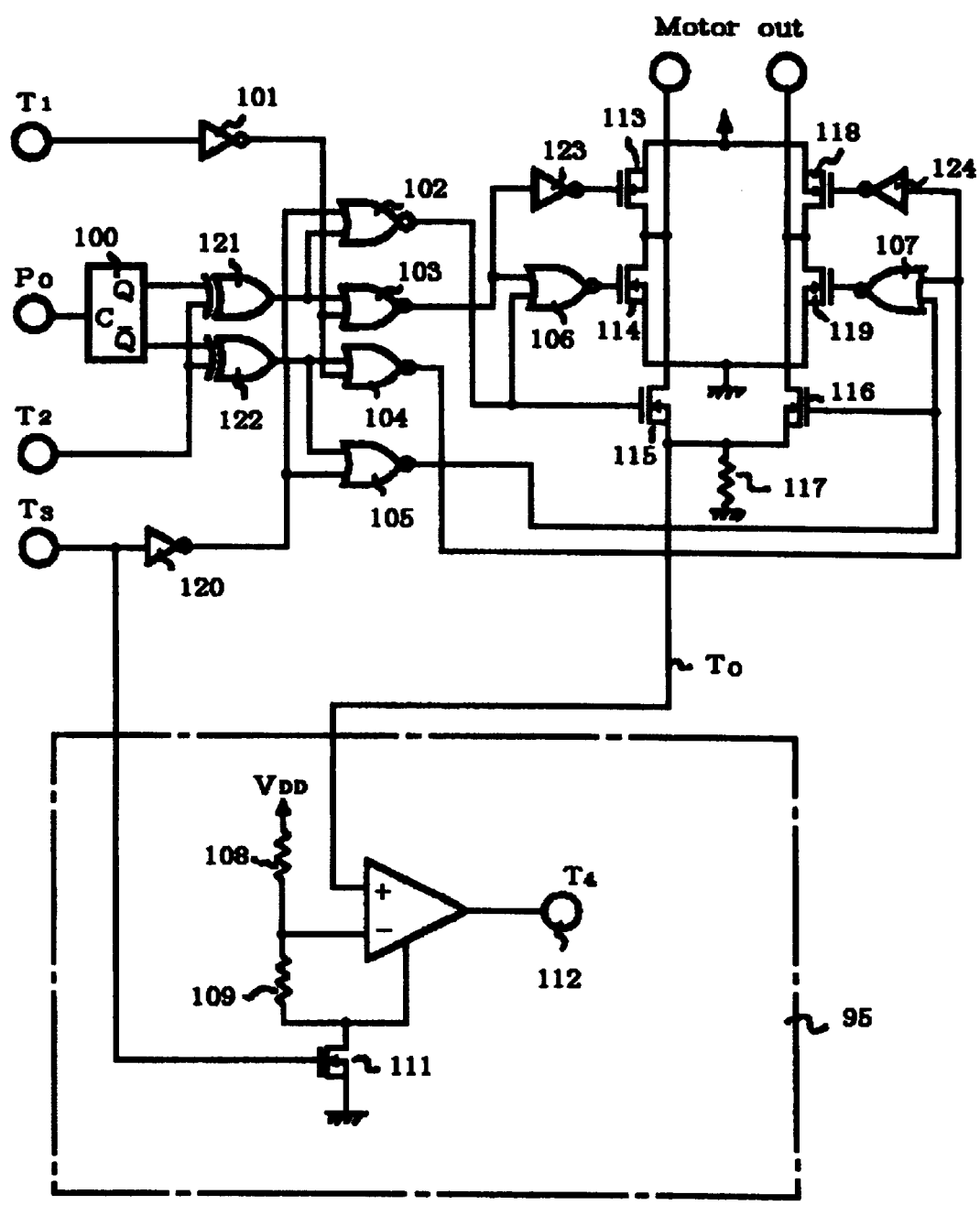
FIG. 22 is a diagram showing the structural example of a driving circuit and a detecting circuit.

FIG. 22 is a circuit diagram showing the drive circuit 94 and the detecting circuit 95 shown in FIG. 20 and an input terminal T1 is an output of the control circuit 93 shown in FIG. 20, where a current flows into the step motor 96 only while the T1 terminal is "H" (high level). The T2 terminal inputs the output of the control circuit 93 shown in FIG. 20, and when T2 is set to "H", Q and inversion Q signals of the flip flop 100 are inputted to EX-OR during that period. Therefore, the output of EX-OR becomes negative logic to the output of the flip flop 100 so that the direction of a current that flows in the step motor 96 can be reverted.

In this embodiment, in case of the normal drive pulse and the non-rotation, it is driven by the correction pulse P2, and sequentially the pulse P3 reverse to the pulse P2 is again applied. This is that in the integrated stator motor, in the case of conducting correction drive by P2, the magnetic saturation period of time of the supersaturation magnetic path of the integrated stator is elongated in the subsequent drive pulse so that the executed pulse width is shortened. Therefore, in the case of conducting the correction drive by P2, the inversion pulse P3 is supplied to the coil of the step motor 96, thereby magnetizing the stator in the direction of the driven pulse, and a period of time necessary for saturation of the integrated part is shortened.

The input terminal T3 inputs the output T3 of the control circuit 93 shown in FIG. 20, and using this pulse, the rotation is detected by the induced voltage detecting method after the rotor 6 is rotated as described above.

When the pulse P0 which is 31.25 msec in period is inputted to the flip flop (hereinafter referred to as "F/F") 100, the F/F 100 becomes the F/F that outputs $\frac{1}{64}$ Hz, and its output Q is inputted to the EX-OR 121, and the inversion output Q is inputted to EX-OR 122. Other input terminals of the EX-ORs 121 and 122 are inputted with the T2, and the output of EX-OR 121 is connected to the NOR gates 102 and 103 whereas the output of EX-OR 122 is connected to the NOR gates 104 and 105, respectively.

The output of the NOT gate 101 is inputted to the NOR gates 103 and 104. The output T3 of the control circuit 93 is inputted to the NOR gates 102 and 105 through the NOT gate 120.

The output of the NOR gate 102 is connected to a first input of an NOR gate 106 and an N-MOS-FET 115. The output of the NOR gate 103 is connected to the input of a P-MOS-FET 113 for drive of the step motor 96 and the second input of the NOR gate 106 through the NOR gate 123.

The output of the NOR gate 104 is connected to the input of a P-MOS-FET 118 for drive of the step motor 96 and the first input of a NOR gate 107 through the NOT gate 124. The output of the NOR gate 105 is connected to the second input of the NOR gate 107 and the N-MOS-FET 116. The output of the NOR gate 106 is connected to an N-MOS-FET 114 for drive of the step motor 96, and the NOR gate 107 is connected to an N-MOS-FET 119 for drive of the step motor 96.

A power supply terminal VDD is a positive power supply input terminal, and connected with the sources of the P-MOS-FETs 113 and 118.

The sources of the N-MOS-FETs 114 and 119 are grounded, and the drains of the P-MOS-FET 113 and the N-MOS-FET 114 are connected to each other, and also connected to the output terminal of the coil of the step motor 96 and the drain of the detection N-MOS-FET 115.

The P-MOS-FET 118 and the N-MOS-FET 119 are connected to each other at their drains, and also connected to the other output terminal of the coil of the step motor 96 and the drain of the detection N-MOS-FET 116.

The N-MOS-FETs 115 and 116 are connected to a source electrode, and its node is connected to one end of the resistor 117. Also, the other end of the resistor 117 is grounded.

The above node of the N-MOS-FETs 115 and 116 and the resistor 117 are connected to a positive input of the comparator 110.

Also, the node T0 represents the rotation/non-rotation signal of the rotor 6, and the comparator 110, the resistors 108, 109, and the N-MOS-FET 111 constitute a detecting circuit 95. When the detection signal T0 sufficiently enables the detection even if the threshold voltage of the C-MOS gate circuit is used, the C-MOS-NOT gate can be used.

The resistor 108 is connected to the power supply voltage VDD, and its other end is connected to the resistor 109, and its node is connected to minus input terminal of the comparator 110. The other end of the resistor 109 is connected to the drain of the detection prohibition N-MOS-FET 111, and grounded through the source. The grounded terminal of the comparator 110 is connected to the drain of the N-MOS-FET 111 and located through the source.

The output of the comparator 110 outputs the signal T4 to the terminal 112 and is inputted to the control circuit 93.

The comparator used in the control circuit 93 of the present invention is a comparator made up of C-MOS, and its operation will be briefly described.

Figure 23A:
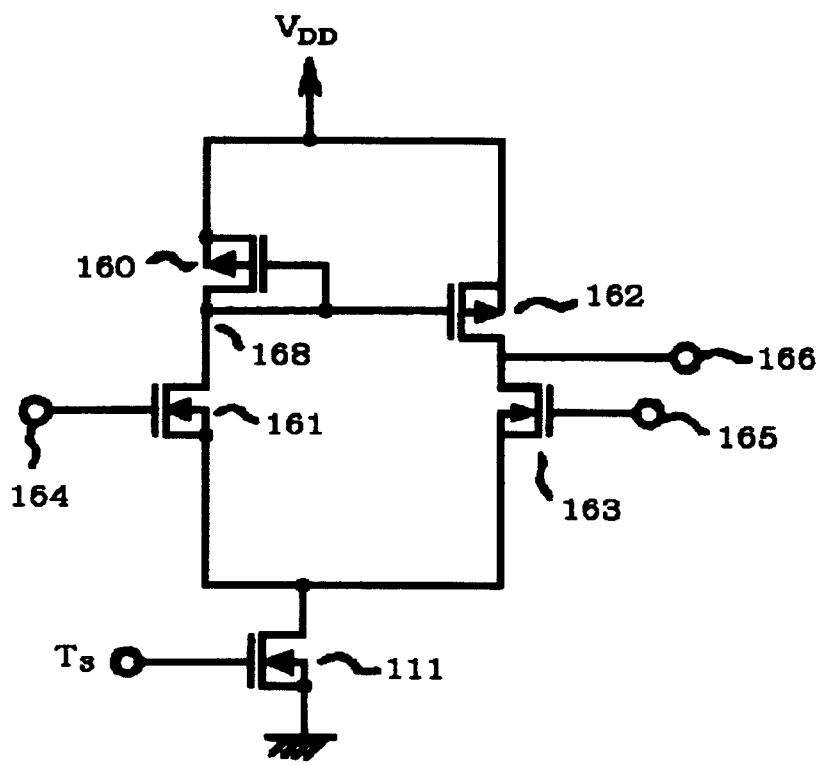
FIGS. 23A and 23B are a detailed structural diagram and a block diagram showing a comparator, respectively.
Figure 23B:
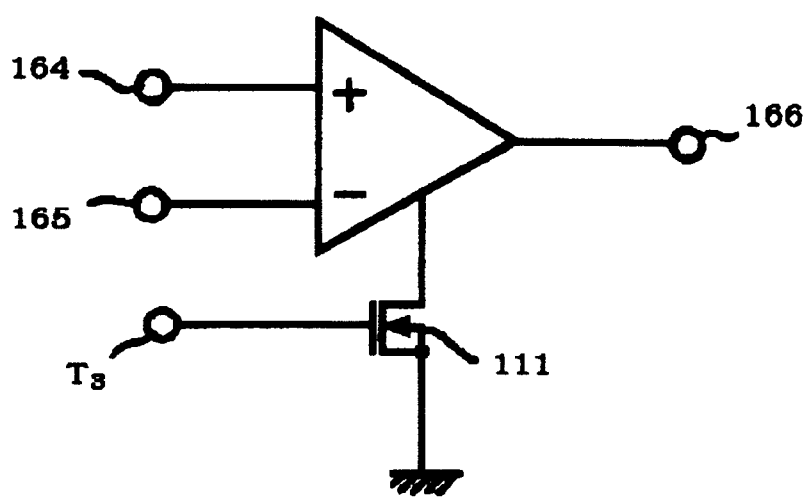

FIGS. 23A and 23B show an example of the comparator 110, in which FIG. 23A is a detailed explanatory diagram thereof, and FIG. 23B is a block diagram thereof.

A terminal 164 is a position input terminal, a terminal 165 is a negative input terminal, and a terminal 166 is an output terminal and the terminal T3 is an enable terminal.

Those function is shown in FIG. 26.

The VDD is a power supply terminal, and connected to the source electrodes of the P-MOS-FETs 160 and 162, respectively.

The gate of the P-MOS-FET 160 is connected to the drain electrode, and its node is connected to the gate of the P-MOS-FET 162 and the drain of the N-MOS-FET 161, respectively.

The gate of the N-MOS-FET 161 is connected to the terminal 164, and its source is connected to the drain of the N-MOS-FET 111. The drain of the P-MOS-FET 162 is connected to the drain of the N-MOS-FET 163 and the output terminal 166. The gate of the N-MOS-FET 163 is connected to the terminal 165, and its source is connected to the source of the N-MOS-FET 161 and the drain of the N-MOS-FET 111.

The source of the N-MOS-FET 111 is grounded, and its gate is connected to the terminal T3. Also, the characteristics of the N-MOS-FETs 161 and 163 are equal to each other, and also the characteristics of the P-MOS-FETs 160 and 162 are equal to each other.

The operation of the comparator thus structured will be described. When the enable terminal T3 is "L", the N-MOS-FET 111 is turned off, and the comparator is not operated.

When the enable terminal T3 becomes "H", the N-MOS-FET 111 is turned on, and the comparator is operated. Also, in this embodiment, because a threshold value of the detection signal is obtained by divided voltage of the resistors 108 and 109, since a power is consumed if the current always flows, only when the pulse T3 becomes "H" by the N-MOS-FET 111, the current is allowed to flow, to thereby reduce the current in the circuit. When the input voltage V1 is applied to the terminal 164, the potential and current of the node 168 are represented as shown in FIG. 24A.

Figure 24A:
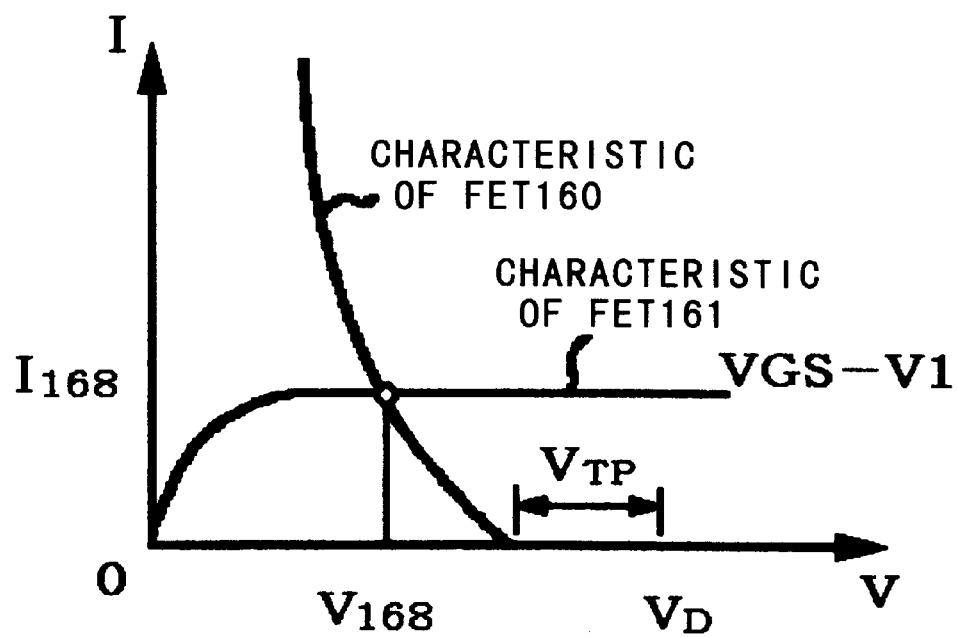
FIGS. 24A and 24B are explanatory diagrams showing the operation of the comparator, respectively.

In FIG. 24A, V168 is a potential of the terminal 168, and I168 is a current that flows in the terminal 168.

Because the gate of the P-MOS-FET 162 is applied with the above V168, its saturation current is equal to I168. This appearance is represented by the characteristic of 162 in FIG. 24B.

On the other hand, assuming that the voltage applied to the terminal 165 is V2, when V2>V4, the saturation current of N-MOS-FET 163 becomes larger than I168. Accordingly, the potential V166 of the output terminal 166 approaches the level "L".

Figure 24B:
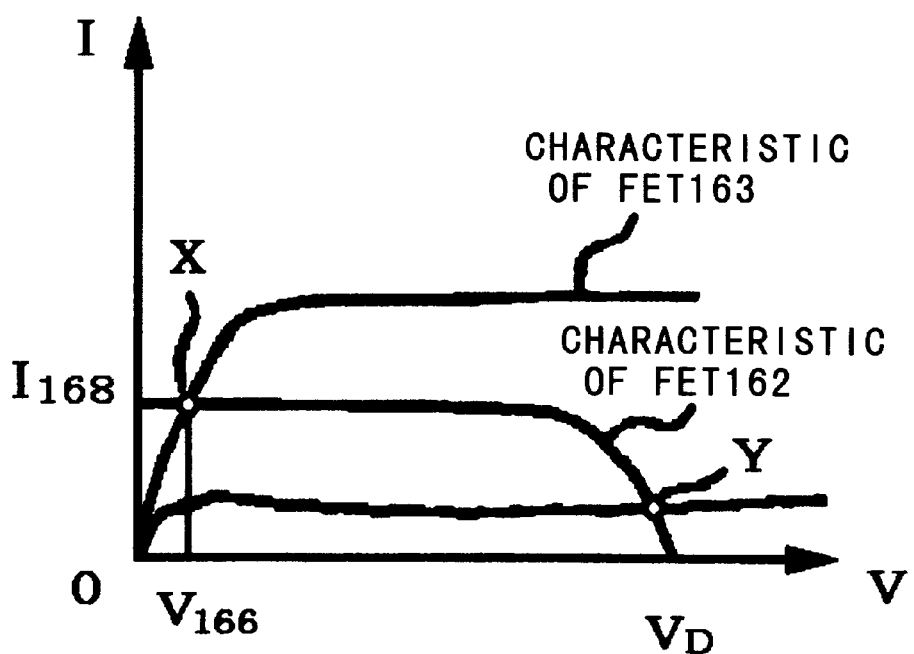

The appearance is indicated by the operation point X in FIG. 24B.

On the contrary, when V2<V1, the output V166 becomes the level "H", and its appearance is indicated by the operation point Y in FIG. 24B. Those functions are shown in FIG. 26.

Figure 25:
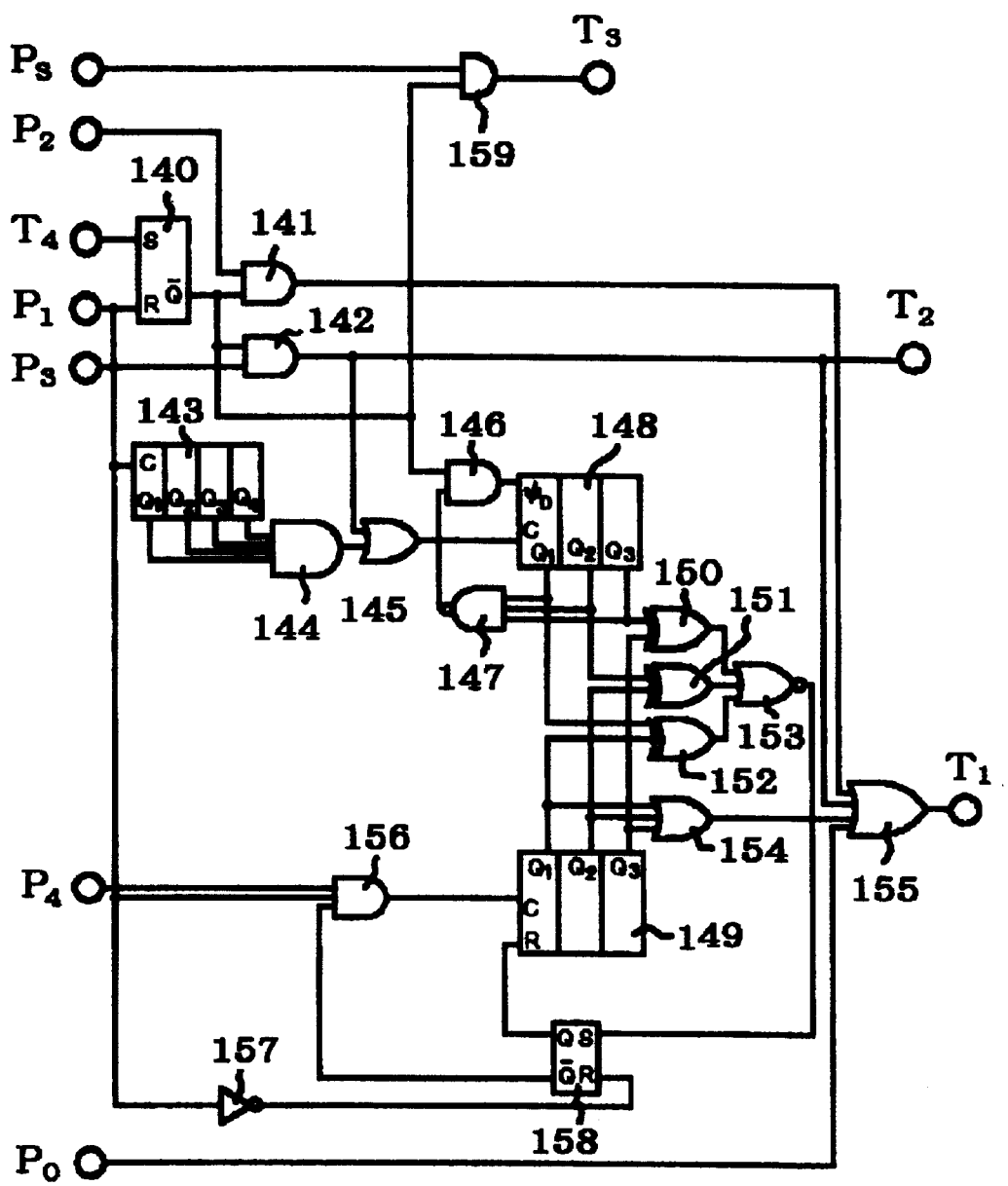
FIG. 25 is a diagram showing a structural example of a control circuit.

FIG. 25 is a circuit example of the control circuit 93 in FIG. 20.

The output signal T4 from the detecting circuit 95 is inputted to the set input terminal S of the SR-F/F140. A signal P1 from the waveform synthesizing circuit 92 is inputted, through a reset input terminal R of the SR-F/F, a clock input terminal of a binary counter 143, an input terminal of an AND gate 156, and a NOT gate 157, to a reset terminal R of an SR-F/F 158.

An AND gate 141 is inputted with the output signal P2 of the waveform synthesizing circuit 92 and an inversion Q output of the SR-F/F140. An AND gate 142 is inputted with an output P3 of the waveform synthesizing circuit 92 and the inversion Q output of the SR-F/F 140, and the output signal is inputted to the drive circuit as the T2. An AND gate 159 is inputted with an output P5 of the waveform synthesizing circuit and the inversion Q of the SR-FF, and its output signal T3 is inputted to the drive circuit 94.

A binary counter 143 is made up of four flip flops in an example shown in the figure, and an output signal at each flip flop is inputted to an AND gate. The output of an AND gate 144 and the output of an AND gate 142 is inputted to an OR gate 145.

An AND gate 146 is inputted with the inversion Q output of the SR-F/F and the output of a NAND gate 147. A U/D input (up/down control input) of an up/down counter 148 is inputted with the output of the AND gate 146, and a clock input C is inputted with the output of an OR gate 145. In this structural example, the up/down counter 148 has three flip flops, and outputs Q1, Q2 and Q3 are inputted to an NAND gate 147, respectively, and also to EX-OR gates 150, 151 and 152, respectively.

An AND gate 156 is inputted with the outputs P0 and P1 of the waveform synthesizing circuit 92 and the inversion Q output of the SR-F/F. The clock input C of a binary counter 149 is inputted with the output of an AND gate 159 and its reset input R is inputted with the output Q of an SR-F/F 158.

In this embodiment, the binary counter 149 has three flip flops, and the respective outputs Q1, Q2 and Q3 are inputted to an OR gate 154, respectively, and also to EX-OR gates 150, 151 and 152, respectively. An NOR gate 153 is inputted with the outputs of the EX-OR gates 150, 151 and 152, and its output is inputted to the reset input S of an SR-F/F158. The OR gate 155 is inputted with the output of an AND gate 141 and the output of the AND gate 142, the output of the OR gate 154, and the output P0 of the waveform synthesizing circuit 92, respectively, and the output T1 is inputted to the drive circuit.

Then, the operation of the control unit 103 thus structured will be described.

The SR-F/F 140 becomes in a set state by inputting a detection signal T4 when the rotor 6 rotates so that the inversion Q becomes "L". Therefore, all of the outputs of the AND gates 141, 142, 146 and 159 become "L". For that reason, the output T3 of the AND gate 159 and the output P3 signal of the waveform synthesizing circuit become the signal "L" simultaneously when the image inversion is detected, and thereafter the detecting circuit is prohibited. Also, because the U/D input of the up/down counter 148 becomes an up counter when it is "H" and a down counter when it is "L", it becomes a down counter when the rotor 6 rotates.

In this situation, because the clock input C of the binary counter 143 is inputted with the output P1 from the waveform synthesizing circuit every 31.25 msec, the output of the AND gate 144 becomes "H" every 1 second and inputted to the clock input C of the up/down counter 148 through the OR gate 145 in case of the above four-flip-flop structure so that the count contents of the up/down counter 148 are reduced by one every one second.

On the other hand, because the output P4 of the waveform synthesizing circuit 92 is a signal of 1024 Hz, the period is about 0.98 msec, and only when the output P1 of the waveform synthesizing circuit 92 is "H", it is inputted to the clock input C of the binary counter 149 through the AND gate 156. In this embodiment, the binary counter 149 is made up of three flip flops.

The EX-ORs 150, 151 and 152 always monitor that the outputs of the binary counter 149 and the up/down counter 148 are identical with each other, and when their contents are identical with each other, all of the outputs of the EX-OR become "L", and the output of the NOR gate 153 becomes "H". Also, the SR-F/F158 is made in a set state, and the output Q becomes "H" so that the binary counter 149 is reset. For that reason, the output of the OR gate 154 is outputted so that the signal of a time width is "H" by the product of the number of counts of the up/down counter and 0.98 msec.

On the other hand, in the case where the output T0 of the detecting circuit 95 is not the signal "H" within the time of detection at all, it is judged that the rotor 6 cannot be rotated by an initial drive pulse, and the inversion Q output of the SR-F/F140 continues the state of "H". For that reason, the output of the AND gate 141 conducts the correction drive of the motor such that the output T2 from the waveform synthesizing circuit 92 is the output of the OR gate 155 as it is.

Also, the output of the AND gate 142 is outputted to the output signal P3 of the waveform synthesizing circuit 92, and then inputted to the drive circuit 94 as the signal T2. In this situation, it is controlled in such a manner that a current flows in a direction opposite to the direction of a current flowing in the coil of the step motor 96 which is in the correction drive state, and the output T1 of the OR gate 155 is inputted to the drive circuit 94. As a result, the influence of the residual magnetism of step motor 96 can be removed, and the supersaturation magnetic path saturation time in case of the integrated stator is erased.

Further, because the inversion Q output of the SR-F/F140 is "H", the output of the AND gate 146 becomes "H", and the U/D input of the up/down counter 148 becomes "H". The up/down counter 148 is set to the up counter, and the output P3 of the waveform synthesizing circuit 92 is inputted to the clock input C of the up/down counter 148 through the AND gate 142 and the OR gate 145.

For that reason, the count contents of the up/down counter 148 becomes +1, and the length of the drive pulse outputted at the next time is elongated by 0.98 msec. All of the outputs Q1, Q2 and Q3 of the flip flop of the up/down counter 148 become "H", when an up input is accepted at the next time, all of the contents of the counter become "L". In order to prohibit this, when all of the inputs of the NAND gate 147 become "H", the output of the AND gate 146 is set to "L", and the up/down counter 148 is set as the down counter to prohibit all of the inputs from being "L".

The output P0 of the waveform synthesizing circuit is provided to decide the minimum pulse width of the normal drive pulse. This is because when the pulse width is started from 0 msec, the energy loss is large until the motor is driven by a constant pulse width, and in this embodiment, the minimum drive pulse width is set to about 4.88 msec.

In the up/down counter 148, the count contents are not reset by reset of the dividing circuit 91, and the drive pulse width before reset is started even after the reset is released.

When the drive pulse of the step motor 96 is short in pulse width to the degree that the step motor 96 cannot be rotated, the actuating lever 110 cannot be rotationally driven without any change of the normal drive pulse width. Accordingly, because the output signal T4 from the detecting circuit is a signal "L", the inversion Q output of the SR-F/F 140 is "H", and the output signal P2 of the waveform synthesizing circuit 92 is supplied to the step motor 96. The pulse width is set to a width that can ensure the maximum torque of the motor. In this embodiment, the width is set to 11.7 msec.

Then, when the output P3 of the waveform synthesizing circuit 92 is inputted, because the up/down counter 148 is an up counter, the contents of count become +1. Accordingly, in the case where the drive pulse width of first one sec. is 4.88 msec, the normal drive pulse of a second sec. becomes a drive pulse having the output of the waveform synthesizing circuit T1=4.88 msec, and a length of 0.98 msec, that is, the length of 5.86 msec.

Further, when the it cannot be rotated by that pulse width, the correction drive of 11.7 msec is conducted. The pulse width of 11.7 msec is set as a pulse width that enables the step motor 96 to be driven stably even if the load of the wheel train of the actuating lever 110 becomes heavy, etc.

Thereafter, the counter of the up/down counter is set to 2 by the output T3 of the waveform synthesizing circuit 92. At the second pulse, the length of the normal drive pulse becomes 6.84 msec.

If the rotor cannot be rotated by that pulse width, the same operation is repeated, and the normal drive pulse width can conduct the drive at a pulse width close to the limit that the rotor 6 can rotate. However, when the counter contents of the binary counter 143 becomes 16, the output of the AND gate 144 becomes "H", and the contents of the up/down counter 148 becomes −1. For that reason, in the case where the normal drive is conducted, for example, at 7.81 msec, the next normal drive pulse becomes 6.84 msec.

Accordingly, in the case where the rotor can be rotated at 6.84 msec, the drive continues at 6.84 msec as it is, but in the case where the rotor cannot be rotated at 6.84 msec, the rotor is driven at 6.84 msec to detect that the rotor is in the non-rotation state, and the rotor 6 is allowed to rotate by the correction drive pulse so that the contents of the up/down counter are set to +1, and the length of the next normal drive pulse becomes 7.81 msec again.

Then, in case of the above pump unit 102, both of the rollers 117a and 117b disposed on both ends of the actuating lever 110 are in contact with the supply tube 106 in a range of about 210 degrees of one rotation 360 degrees so that a given load is applied to the step motor 96. On the other hand, in a range of the remaining 150 degrees, because the supply tube 106 is in contact with only one of the rollers 117a and 117b, the load is lightened. In this way, the load is varied even during one rotation, and even if the load is finely varied at the respective positions, the rotor 6 can be driven at the smallest drive pulse width by which the rotor 6 can always rotate using the normal drive pulse and the correction drive pulse as described above so that the pump unit 102 can be driven in a state where the power consumption of the step motor 96 is at the minimum.

In this embodiment, because the binary counter 143 is a binary counter having four flip flops, the drive pulse and the normal drive pulse can be outputted at the same time once per one second. For that reason, in the case where the power is intended to be further reduced, the number of stages in the binary counter 143 is further increased, thereby being capable of reducing the possibility that both of the normal drive pulse and the correction drive pulse are generated within one second.

However, if the number of stages of the counter is too increased, the load is increased, as a result of which after the pulse width of the normal drive is caused to be elongated, it takes time to return the pulse width to the original pulse width when the load is reduced. For that reason, it is nonsense that the number of stages in the binary counter is too large.

Subsequently, the experimental result of the present invention will be described.

The step motor 96 of the implant-type chemical supply device as used is 2.4 mm in diameter of the rotor 6, 0.7 mm in thickness, 0.3 mm in interval between the stator and the rotor 6, 1.5 kΩ in resistance of the coil, and 9000 turns in the number of turns of the coil.

FIG. 27 shows experimental values of a current when the step motor 96 was driven at each pulse and those of an output torque measured by the actuating lever, and the measurement of at how rate each pulse of P1 and P2 occurred when the step motor 96 was assembled with the above implant-type chemical supply device and then operated for one day. In the example, when one of pulses P1 was continuously supplied at 64 pulses to the step motor 96, the pulse width is set so as to be shortened one step. Under those circumstances, the experiment was conducted.

That is, a sum of the rate at which each pulse occurred and the product of current in FIG. 27 is a mean current of the implant-type chemical supply device in one day. As a result of calculation, the value was 320 μA. Although the step motor 96 was originally designed to be driven at the pulse width of 9.77 msec, regardless the implant-type chemical supply device according to the present invention with the performance which is not different from the conventional one, the current could be reduced from 520 μA to 320 μA, that is, reduced by 62%.

In the above embodiment, the control circuit 93 supplies the normal drive pulse or the correction drive pulse to the step motor 96 on the basis of the rotating state of the step motor 96, and also when no non-rotation signal is generated, the drive pulse having the effective power smaller by one than the past normal drive pulse is supplied to the step motor 96. However, in the structure of the pump unit 102 of the implant-type chemical supply device, the supply tube 106 is arranged to be substantially U-shaped, and the actuating lever 110 which is in contact with the supply tuber 106 is designed in such a manner that one of the rollers 117a and 117b fitted on one end of the actuating lever 110 is away from the supply tube 106 in a range of a predetermined angle of one rotation, that is, 360 degrees (about 150 degrees in the drawing), and it is apparent that the load is greatly lightened in comparison with other range of 210 degrees in a period when it passes the range of the predetermined angle. In other words, it is apparent that the magnitude of the load is periodically changed.

With such a structure, it may be controlled in such a manner that in the range of 210 degrees where both of the rollers 117a and 117b of the actuating lever 110 are in contact with the supply tube 106, the drive pulse which is larger in effective power is outputted, but in the range of 150 degrees where only one of the rollers 117a and 117b of the actuating lever 110 is in contact with the supply tube 106, the drive pulse which is smaller in effective power is outputted.

Figure 28:
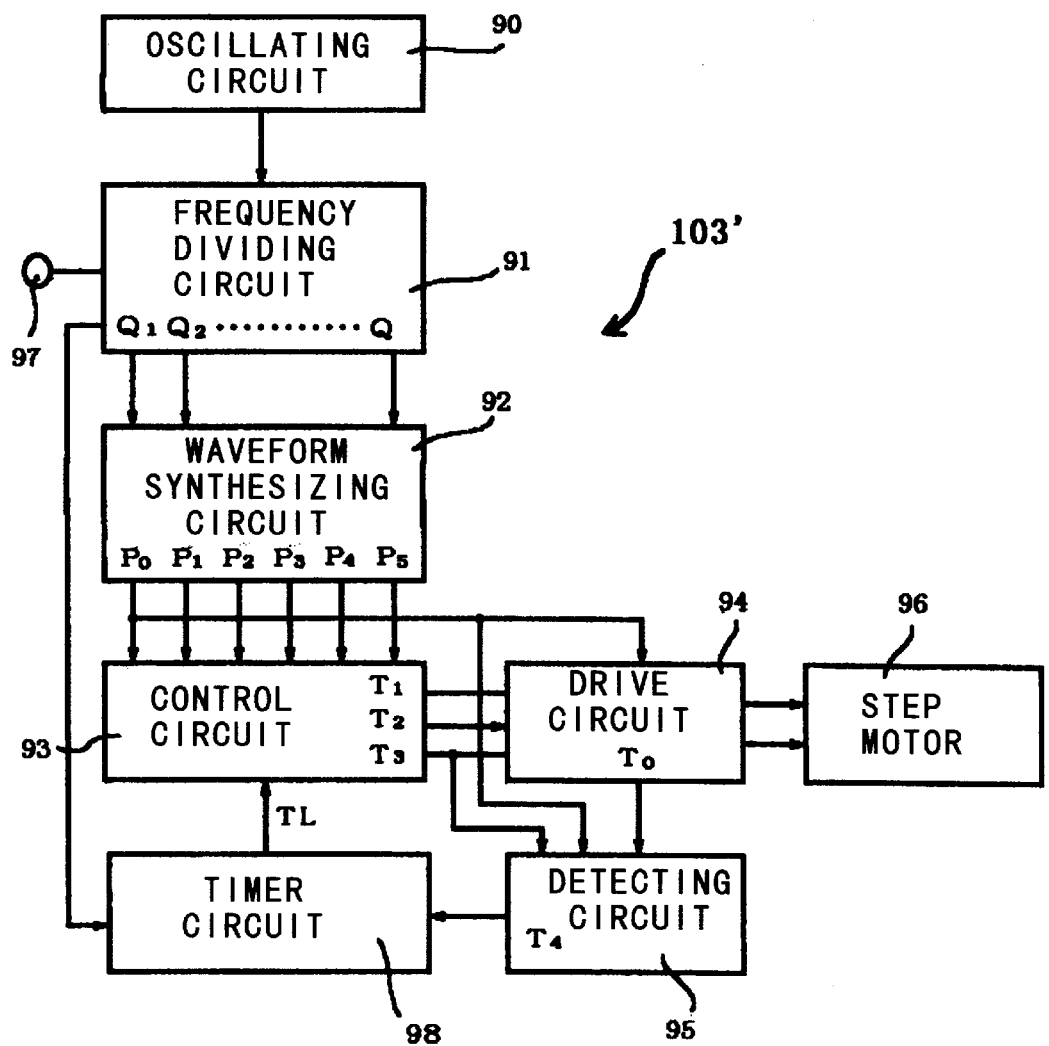
FIG. 28 is a block diagram showing another structural example of the present invention.

FIG. 28 shows a modified example of the structure of the control unit 103 shown in FIG. 20 in a case where the above idea is applied.

Control means 103' shown in FIG. 28 is provided with a timer 98 which is responsive to an output T4 from the detecting circuit 95, and responsive to such a condition that the actuating lever 110 is in a light-load state, that is, the condition that the actuating lever 110 falls within the range of 150 degrees where only one of the rollers 117a and 117b of the actuating lever 110 is in contact with the supply tube 106, to start the counting operation of the frequency dividing pulses from the frequency dividing circuit 91. Then, a light-load signal TL is outputted from the timer 98 together with the start of the counting operation, whereby the control circuit 93 is controlled so as to output the drive pulse of a predetermined pulse width for a light load which is narrower than the width of the normal drive pulse. As a result, the small drive pulse in effective power which is suited for the light-load state of the actuating lever 110 is outputted from the control circuit 93.

Since the rotating angle range where the actuating lever 110 is in a predetermined light-load state is found in advance, the timer 98 continues the above-described control state of the control circuit 93 until the number of pulses suited for the above state are completely counted. The output of the light-load signal TL from the timer 98 is suspended at a timing when the predetermined light-load operation state of the actuating lever 110 is completed, and the larger drive pulse in effective power is again outputted from the control circuit 93.

In this way, when only one of the rollers 117a and 117b is in contact with the supply tube 106 so that the load on the pulse motor 96 is lightened, if the actuating lever 110 is rotationally driven by the smaller drive pulse in effective power, and the larger drive pulse in effective power is again outputted by time up of the timer 98, the power consumption of the step motor 96 is further reduced so as to drive the pump unit 102. Also, since the state of the drive pulse is surely changed over in response to the range of the rotating angle of the actuating lever 110, useless power consumption can be surely prevented without being adversely affected by noises or the like.

In the structure shown in FIG. 28, when the step motor 96 starts the light-load operation, the counting operation of the timer circuit 98 is started to output the light-load signal TL from the timer circuit 98 so that the output of the drive pulse from the control circuit 93 is controlled. Alternatively, the normal load of the step motor 96, that is, the normal load signal representing a period of the state where both of the rollers 117a and 117b of the actuating lever 110 press the supply tube 106 is outputted from the timer circuit 98, to thereby control the output of the drive pulse from the control circuit 93.

The step motor 96 as described in the above-mentioned embodiment is of the integrated stator motor. However, the same great effects can be obtained without any change in the effects even if other motors including the two-body stator motor are used.

Although the waveform of the drive pulse as described in the above embodiment is rectangle in shape, it may be comb-shaped waveform where the rectangular waveforms are thinned out, and the same great effects can be obtained without any change in the effects.

As was described above, according to the present invention, all elements of the device are made up of structural elements which can be built in a C-MOS-IC, and the step motor is always driven by the minimum pulse width that enables the step motor to be driven. Therefore, there is no factors of increasing the costs, and the general-purpose motors can be driven with the minimum power consumption. Also, the device can be thinned, downsized and reduced in the costs, with the result that the implant-type chemical supply device provides very great advantages.

The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An implant-type chemical supply device, comprising:
a pump unit having a supply tube for supplying chemicals from a chemical tank, and an actuating lever which is rotated by a step motor having a device coil and has rollers on both ends thereof so that said rollers are arranged in contact with the halfway of said supply tube, for extruding the chemicals within said supply tube by said rollers to supply the chemicals;
a waveform synthesizing circuit for producing drive pulse groups each having a different effective power;
a drive circuit for supplying any one of the drive pulse groups to the step motor in synchronism with a time signal;
a detection circuit for generating a non-rotation signal when an induced voltage developed in said drive coil within said step motor by free oscillations of said step motor is equal to or less than a given value after the drive pulse is supplied to said step motor; and
a control circuit for controlling said drive circuit so that the drive pulse having an effective power larger by one in magnitude than that of the drive pulse during non-rotation is supplied to said step motor when the non-rotation signal is generated, and the drive pulse having an effective power smaller by one in magnitude than that of the past drive pulse during non-rotation is supplied to said step motor when no non-rotation signal is generated for a predetermined period of time.

2. An implant-type chemical supply device, comprising:
a pump unit for supplying chemicals from a chemical tank having a supply tube a part of which is disposed in the form of an arc to form an arcuate portion, and an actuating lever which is rotated by a step motor having a device coil and has rollers on both ends thereof so that the rollers are arranged to be in contact with the arcuate portion of the supply tube only in a range of predetermined angles when the actuating lever is rotated, for extruding the chemicals within the supply tube by the rollers to supply the chemicals;
a waveform synthesizing circuit for producing drive pulse groups each having a different effective power;
a drive circuit for supplying any one of the drive pulse groups to the step motor in synchronism with a time signal;
a detection circuit for generating a non-rotation signal when an induced voltage developed in the drive coil within the step motor by free oscillations of the step motor is equal to or less than a given value after the drive pulse is supplied to the step motor;
a timer circuit for outputting a light-load signal indicative of a period of time when the rollers are apart from the supply tube in response to the non-rotation signal; and
a control circuit for controlling the drive circuit so that the drive pulse having a larger effective power is supplied to the step motor when no light-load signal is outputted, and the drive pulse having a smaller effective power is supplied to the step motor when the light-load signal is outputted.

* * * * *

UNITED STATES PATENT AND TRADEMARK OFFICE
CERTIFICATE OF CORRECTION

PATENT NO.   : 6,264,634 B1
DATED        : July 24, 2001
INVENTOR(S)  : Ko Yamazaki It is certified that error appears in the above-identified patent and that said Letters Patent is hereby corrected as shown below:

<u>Title page,</u>
In the heading, insert:
-- Foreign Application Priority Data
July 25, 1997 [JP] Japan . . .9-20059 --.

Signed and Sealed this

Twenty-sixth Day of February, 2002

*Attest:*

*Attesting Officer*

JAMES E. ROGAN
*Director of the United States Patent and Trademark Office*